(12) United States Patent
Kolstad

(10) Patent No.: US 9,862,627 B2
(45) Date of Patent: Jan. 9, 2018

(54) WATER TREATMENT DEVICE AND METHODS OF USE

(71) Applicant: Silver Bullet Water Treatment Company, LLC, Denver, CO (US)

(72) Inventor: David Kolstad, Denver, CO (US)

(73) Assignee: SILVER BULLET WATER TREATMENT COMPANY, LLC, Denver, CO (US)

( * ) Notice: Subject to any disclaimer, the term of this patent is extended or adjusted under 35 U.S.C. 154(b) by 0 days.

(21) Appl. No.: 15/448,082

(22) Filed: Mar. 2, 2017

(65) Prior Publication Data

US 2017/0197856 A1 Jul. 13, 2017

Related U.S. Application Data

(63) Continuation of application No. 14/866,484, filed on Sep. 25, 2015, now Pat. No. 9,617,177, which is a
(Continued)

(51) Int. Cl.
*A61N 5/00* (2006.01)
*G01N 23/00* (2006.01)
(Continued)

(52) U.S. Cl.
CPC ............. *C02F 1/722* (2013.01); *C01B 13/10* (2013.01); *C02F 1/32* (2013.01); *C02F 1/78* (2013.01);
(Continued)

(58) Field of Classification Search
CPC ..................................... A61L 2/00; C02F 1/00
(Continued)

(56) References Cited

U.S. PATENT DOCUMENTS

| 4,141,830 A | 2/1979 | Last |
| 4,207,286 A | 6/1980 | Gut Boucher |

(Continued)

FOREIGN PATENT DOCUMENTS

| CN | 1185714 | 6/1998 |
| CN | 2725280 | 9/2005 |

(Continued)

OTHER PUBLICATIONS

"Concise Description of the Relevance of U.S. Pat. No. 5,622,622 (Johnson) to Pending U.S. Appl. No. 13/688,027 (Kolstad)," submitted under 37 CFR 1.290 in U.S. Appl. No. 13/688,027 on Oct. 23, 2013, 8 pages.

(Continued)

*Primary Examiner* — Monzer R Chorbaji
(74) *Attorney, Agent, or Firm* — Sheridan Ross PC

(57) ABSTRACT

A water treatment device and methods of treating water such as cooling tower water, agricultural water, water used in the production of oil and/or gas, swimming pool water, and hot tub or spa water, are described. The water treatment device utilizes ultraviolet radiation, a magnetic field, and ozone fortified air to treat the water, typically resulting in reduced microbial contamination and reduced alkalinity in cooling tower water. Cooling tower water may consequently be run at higher cycles of concentration while reducing or eliminating deposition of minerals on cooling tower components. Swimming pool water and hot tub water treated with the water treatment device typically requires less chlorine, and chlorine levels are typically more stable than without the device.

20 Claims, 12 Drawing Sheets

Related U.S. Application Data continuation of application No. 13/688,027, filed on Nov. 28, 2012, now Pat. No. 9,187,344, which is a continuation-in-part of application No. 12/534,761, filed on Aug. 3, 2009, now Pat. No. 8,361,384, said application No. 13/688,027 is a continuation-in-part of application No. 13/444,697, filed on Apr. 11, 2012, now Pat. No. 9,321,665.

(60) Provisional application No. 61/085,419, filed on Aug. 1, 2008, provisional application No. 61/474,646, filed on Apr. 12, 2011.

(51) Int. Cl.

| | | |
|---|---|---|
| *B01D 17/06* | (2006.01) | |
| *C02F 1/72* | (2006.01) | |
| *C02F 1/32* | (2006.01) | |
| *C02F 9/00* | (2006.01) | |
| *C01B 13/10* | (2006.01) | |
| *C02F 1/78* | (2006.01) | |
| *A61N 5/06* | (2006.01) | |
| *C02F 1/48* | (2006.01) | |
| *C02F 103/02* | (2006.01) | |
| *C02F 103/36* | (2006.01) | |

(52) U.S. Cl.
CPC .............. *C02F 9/00* (2013.01); *A61N 5/0624* (2013.01); *C02F 1/325* (2013.01); *C02F 1/48* (2013.01); *C02F 1/481* (2013.01); *C02F 1/727* (2013.01); *C02F 2103/023* (2013.01); *C02F 2103/365* (2013.01); *C02F 2303/04* (2013.01); *Y02W 10/37* (2015.05)

(58) Field of Classification Search
USPC ............... 422/24, 905; 250/455.11, 492.1; 210/748, 748.03, 748.1, 748.11
See application file for complete search history.

(56) References Cited

U.S. PATENT DOCUMENTS

| | | | |
|---|---|---|---|
| 4,220,529 A | | 9/1980 | Daude-Lagrave |
| 4,230,571 A | | 10/1980 | Dadd |
| 4,422,933 A | | 12/1983 | Sverre et al. |
| 4,458,153 A | | 7/1984 | Wesley |
| 4,524,079 A | | 6/1985 | Hofmann |
| 4,562,014 A | | 12/1985 | Johnson |
| 4,655,933 A | | 4/1987 | Johnson et al. |
| 4,836,929 A | | 6/1989 | Baumann |
| 4,857,204 A | * | 8/1989 | Joklik .................. C02F 1/02 204/155 |
| 4,906,387 A | | 3/1990 | Pisani |
| 5,130,032 A | | 7/1992 | Sartori |
| 5,145,585 A | | 9/1992 | Coke |
| 5,207,921 A | | 5/1993 | Vincent |
| 5,217,607 A | | 6/1993 | Dalton, III |
| 5,223,105 A | | 6/1993 | Arthurson |
| 5,364,536 A | | 11/1994 | Mercier |
| 5,419,816 A | | 5/1995 | Sampson |
| 5,424,032 A | | 6/1995 | Christensen |
| 5,556,958 A | | 9/1996 | Carroll |
| 5,595,666 A | | 1/1997 | Kochen |
| 5,622,622 A | | 4/1997 | Johnson |
| 5,662,803 A | | 9/1997 | Young |
| 5,665,762 A | | 9/1997 | Carroll |
| 5,675,153 A | | 10/1997 | Snowball |
| 5,685,994 A | | 11/1997 | Johnson |
| 5,732,654 A | | 3/1998 | Perez et al. |
| 5,750,072 A | | 5/1998 | Sangster |
| 5,753,106 A | | 5/1998 | Schenck |
| 5,780,860 A | | 7/1998 | Gadgil |
| 5,871,620 A | | 2/1999 | Haug |
| 5,879,546 A | | 3/1999 | Burford |
| 5,997,812 A | | 12/1999 | Burnham |
| 6,090,294 A | | 7/2000 | Teran |
| 6,117,335 A | | 9/2000 | Bender |
| 6,303,085 B1 | | 10/2001 | Kwak et al. |
| 6,419,821 B1 | | 7/2002 | Gadgil |
| 6,468,433 B1 | | 10/2002 | Tribelski |
| 6,469,308 B1 | | 10/2002 | Reed |
| 6,555,011 B1 | | 4/2003 | Tribelsky |
| 6,673,248 B2 | | 1/2004 | Chowdhury |
| 6,682,697 B2 | | 1/2004 | He |
| 6,730,205 B2 | | 5/2004 | Holland |
| 6,740,245 B2 | | 5/2004 | Johnson |
| 6,752,923 B1 | | 6/2004 | Jans |
| 6,780,328 B1 | | 8/2004 | Zhang |
| 6,863,826 B2 | | 3/2005 | Sheets |
| 6,986,867 B2 | | 1/2006 | Hanley |
| 6,991,735 B2 | | 1/2006 | Martin |
| 7,118,852 B2 | | 10/2006 | Purdum |
| 7,140,323 B2 | | 11/2006 | Ashworth et al. |
| 7,267,778 B2 | | 9/2007 | de Meulenaer |
| 7,285,223 B2 | | 10/2007 | Martin |
| 7,481,924 B2 | | 1/2009 | Takahashi |
| 7,531,096 B2 | | 5/2009 | Yarbrough |
| 8,361,384 B1 | | 1/2013 | Kolstad |
| 9,187,344 B2 | | 11/2015 | Kolstad |
| 9,321,665 B2 | | 4/2016 | Kolstad et al. |
| 9,617,177 B2 | | 4/2017 | Kolstad |
| 9,650,270 B2 | | 5/2017 | Kolstad et al. |
| 2002/0139750 A1 | | 10/2002 | Boyce |
| 2002/0170816 A1 | | 11/2002 | Leffler |
| 2002/0172627 A1 | | 11/2002 | Aoyagi |
| 2003/0141260 A1 | | 7/2003 | Corbin |
| 2004/0052680 A1 | | 3/2004 | Elwood |
| 2004/0055965 A1 | | 3/2004 | Hubig |
| 2006/0011558 A1 | | 1/2006 | Fend |
| 2006/0045796 A1 | | 3/2006 | Anderle |
| 2006/0263441 A1 | | 11/2006 | Fukui |
| 2007/0009421 A1 | | 1/2007 | Kittrell et al. |
| 2007/0029261 A1 | | 2/2007 | Chew |
| 2007/0062883 A1 | | 3/2007 | Frederick, Jr. et al. |
| 2007/0125719 A1 | | 6/2007 | Yarbrough |
| 2008/0142452 A1 | | 6/2008 | Denkewica |
| 2008/0292497 A1 | | 11/2008 | Vangeneugden et al. |
| 2009/0286899 A1 | | 11/2009 | Hofmann et al. |
| 2010/0219136 A1 | | 9/2010 | Campbell |
| 2010/0247390 A1 | | 9/2010 | Tanaka et al. |
| 2011/0024361 A1 | | 2/2011 | Schwartzel |
| 2011/0158946 A1 | | 6/2011 | Durvasula et al. |
| 2012/0012536 A1 | | 1/2012 | Klochkoff et al. |
| 2012/0272676 A1 | | 11/2012 | Klochkoff et al. |
| 2015/0125545 A1 | | 5/2015 | Kolstad et al. |
| 2015/0136709 A1 | | 5/2015 | Kolstad et al. |
| 2016/0083275 A1 | | 3/2016 | Kolstad |

FOREIGN PATENT DOCUMENTS

| | | |
|---|---|---|
| EP | 1394118 | 3/2004 |
| EP | 1710209 | 10/2006 |
| WO | WO 96/22944 | 8/1996 |
| WO | WO 97/14301 | 4/1997 |

OTHER PUBLICATIONS

"Concise Description of the Relevance of U.S. Pat. No. 5,685,994 (Johnson) to Pending U.S.Appl. No. 13/688,027 (Kolstad)," submitted under 37 CFR 1.290 in U.S. Appl. No. 13/688,027 on Oct. 23, 2013, 11 pages.

"Concise Description of the Relevance of U.S. Pat. No. 6,740,245 (Johnson) to Pending U.S. Appl. No. 13/688,027 (Kolstad)," submitted under 37 CFR 1.290 in U.S. Appl. No. 13/688,027 on Oct. 23, 2013, 8 pages.

Cano-Gomez et al. "*Vibrio owensii* sp. nov., isolated from cultured crustaceans in Australia." FEMS Microbiology Letters Jan. 2010, vol. 302, No. 2, pp. 175-181.

(56) References Cited

OTHER PUBLICATIONS

Chamberlain, "Challenge: Health Management Program Focuses on 'Perfect Killer' EMS," The Global Aquaculture Advocate, Nov./Dec. 2013, vol. 16, No. 6, p. 14.
Gao et al. "Diversity and pathogenicity of *Vibrio* spp. Populations in Freshwater products in Jiangsu Province," Chinese Journal of Zoonoses, 2013, vol. 29, No. 2, pp. 142-147 (machine translation of abstract only).
Hardman et al. "Quorum sensing and the cell-cell communication dependent regulation of gene expression in pathogenic and non-pathogenic bacteria." Antonie van Leeuwenhoek, Nov. 1998, vol. 74, No. 4, pp. 199-210.
Xie et al. "The Research Advance in Shrimp Vibriosis—Reviewed on shrimp pathogens of vibriosis, pathogenic mechanisms and pathogenic conditions, symptoms and histopathological changes of the disease shrimp, and the elimination mechanisms of shrimp to vibrio," Natural Science Journal of Hainan University, 2007, vol. 25, No. 1, pp. 88-95 (machine translation of abstract only).
International Search Report and Written Opinion for International Application No. PCT/US2012/033097, dated Jun. 29, 2012, 13 pages.
International Preliminary Report on Patentability for International Application No. PCT/US2012/033097, dated Oct. 15, 2013, 7 pages.
Official Action for Canada Patent Application No. 2,803,926, dated Apr. 8, 2015 4 pages.
Official Action for Canada Patent Application No. 2,803,926, dated Oct. 24, 2016 3 pages.
Notice of Allowance for Canada Patent Application No. 2,803,926, dated Jul. 13, 2017 1 page.
Official Action for European Patent Application No. 12719139.3, dated Dec. 16, 2014 6 pages.
Official Action for European Patent Application No. 12719139.3, dated Sep. 29, 2016 5 pages.
Intention to Grant for European Patent Application No. 12719139.3, dated Jul. 27, 2017 55 pages.
Official Action with English Translation for Israel Patent Application No. 228830, dated Dec. 11, 2016 7 pages.
Official Action for Mexico Patent Application No. MX/a/2013/000551, dated Nov. 27, 2014 3 pages.
Official Action with English Translation for Mexico Patent Application No. MX/A/2013/000551, dated May 25, 2015 8 pages.
International Search Report and Written Opinion for International (PCT) Patent Application No. PCT/US14/57213, dated Dec. 15, 2014 10 pages.
International Preliminary Report on Patentability for International (PCT) Patent Application No. PCT/US14/57213, dated May 10, 2016, 7 pages.
International Search Report and Written Opinion for International (PCT) Patent Application No. PCT/US15/15757, dated Apr. 30, 2015 9 pages.
International Preliminary Report on Patentability for International (PCT) Patent Application No. PCT/US2015/015757, dated Mar. 30, 2017 8 pages.
Official Action for U.S. Appl. No. 12/534,761, dated Apr. 27, 2012, 13 pages. .
Notice of Allowance for U.S. Appl. No. 12/534,761, dated Aug. 29, 2012, 7 pages.
Official Action for U.S. Appl. No. 13/688,027, dated Feb. 17, 2015, 10 pages.
Notice of Allowance for U.S. Appl. No. 13/688,027, dated Jun. 25, 2015, 7 pages.
Official Action for U.S. Appl. No. 14/866,484, dated Jul. 15, 2016 10 pages.
Notice of Allowance for U.S. Appl. No. 14/866,484, dated Dec. 2, 2016 7 pages.
Official Action for U.S. Appl. No. 13/444,697, dated Mar. 24, 2015, 10 pages.
Official Action for U.S. Appl. No. 13/444,697, dated Sep. 4, 2015 13 pages.
Notice of Allowance for U.S. Appl. No. 13/444,697, dated Dec. 10, 2015 6 pages.
Official Action for U.S. Appl. No. 15/065,565, dated Apr. 7, 2016, 8 pages.
Official Action for U.S. Appl. No. 15/065,565, dated Oct. 13, 2016 10 pages.
Notice of Allowance for U.S. Appl. No. 15/065,565, dated Jan. 10, 2017 6 pages.
Official Action for U.S. Appl. No. 14/607,973, dated Jun. 12, 2017 13 pages.
Official Action for U.S. Appl. No. 14/617,632, dated Feb. 9, 2016, 14 pages.
Official Action for U.S. Appl. No. 14/617,632, dated Jul. 5, 2016 17 pages.
Official Action for U.S. Appl. No. 14/617,632, dated Apr. 14, 2017 15 pages.
Official Action for U.S. Appl. No. 14/617,632, dated Aug. 18, 2017 18 pages.

* cited by examiner

WATER TREATMENT DEVICE AND METHODS OF USE

CROSS-REFERENCE TO RELATED APPLICATIONS

This application is a continuation of U.S. patent application Ser. No. 14/866,484, filed Sep. 25, 2015, which is a continuation of U.S. patent application Ser. No. 13/688,027, filed Nov. 28, 2012 and issued as U.S. Pat. No. 9,187,344 on Nov. 17, 2015, which is a continuation-in-part of U.S. patent application Ser. No. 12/534,761, filed Aug. 3, 2009 and issued as U.S. Pat. No. 8,361,384 on Jan. 29, 2013, which claims the benefit of U.S. Provisional Patent Application Ser. No. 61/085,419, filed Aug. 1, 2008, and U.S. patent application Ser. No. 13/688,027 is a continuation-in-part of U.S. patent application Ser. No. 13/444,697, filed Apr. 11, 2012 and issued as U.S. Pat. No. 9,321,665 on Apr. 26, 2016, which claims the benefit of U.S. Provisional Patent Application Ser. No. 61/474,646, filed Apr. 12, 2011, the entire disclosure of each of which is hereby incorporated herein by reference.

FIELD

The disclosed invention pertains generally to systems and methods for treating water. More particularly, embodiments of the disclosed invention utilize ultraviolet light and/or magnets to treat water.

BACKGROUND

Water treatment is required to generate or maintain acceptable water quality in systems such as cooling towers, evaporative coolers, heat exchangers, chillers, process recirculation systems, point-of-entry water treatment systems, petroleum and gas production systems, feedlot waters, architectural waters, agricultural waters, recreational waters, hydraulic fracturing waters (for example as used in petroleum and gas producing industries), waters associated with petroleum and gas production (including waters co-produced with petroleum and/or gas, injection waters associated with primary, secondary and tertiary petroleum and/or gas production, and disposal of co-produced waters), flowback waters, and various wastewater treatment systems.

Cooling towers use water as a cooling medium to absorb heat from air conditioning coils or similar heat dumping devices. Water makes an excellent cooling medium due to its relatively high specific heat capacity, its excellent heat conduction in liquid form, and its relatively high heat of vaporization. However, cooling tower water requires extensive treatment to prevent water quality from degrading to unacceptable levels.

Cooling towers that circulate water to dissipate or dispose of heat usually lose substantial quantities of water to evaporation. A typical air conditioning cooling tower loses to evaporation about 3 gallons of water per minute, per 100 tons of air conditioning capacity. A large hospital may have about 1000 tons of air conditioning capacity. Thus the large hospital air conditioning cooling tower loses about 1800 gallons of water per hour through evaporation. Vaporization of cooling tower water leaves behind substantially all of the solids dissolved in the water that becomes vaporized, resulting in increased concentration of dissolved solids in cooling tower water that remains in liquid phase in the tower. Cooling tower water that is hyper-concentrated with solutes (solute laden) and the precipitation or deposition of those solids on cooling tower components is a major problem. Cycle(s) of concentration ("cycle") is a measure of the degree to which dissolved solids concentration in circulating water is increased over that of feed water (also referred to as raw water) as follows: feed water is at 1 cycle of concentration; where dissolved solids in circulating water reach a concentration that is twice that of the feed water, the circulating water is at or has undergone 2 cycles of concentration; at a concentration of 4 times that of feed water, the circulating water is at or has undergone 4 cycles of concentration, etc.

Carbonate precipitation and deposition are typical problems in cooling towers, due at least in part to hyper-concentration of solutes, and to alkalinization. Calcium carbonate and magnesium carbonate are frequently the most common problem species. Carbonate precipitation is exacerbated by highly alkaline cooling tower water because proportions of carbonate to bicarbonate increase with increase in pH, and carbonate is less soluble in water than bicarbonate. Accordingly, a common problem is precipitation of carbonate at higher pH values. Control of alkalinity (i.e. lowering pH) is therefore highly desirable in cooling tower water treatment. Bacterial growth and growth of microorganisms or other organisms in cooling tower water and on cooling tower components is also a substantial problem.

Cooling tower water alkalinity and hyper-concentration of dissolved solids is typically addressed by adding chemicals to the water that help keep the dissolved solids in solution or suspension. However, such chemicals can add substantially to building cooling costs. Chemicals (biocides) are also used to inhibit organism growth, but such chemicals can also be costly, and some biocides are less effective under conditions of increased alkalinity.

Cooling tower water quality is also typically maintained by draining a portion of the water (referred to as bleeding off) and replacing the drained water with feed water that is not hyper-concentrated or substantially biologically contaminated by elevated microorganism levels. Use of chemicals to treat cooling tower water can complicate bleeding off, or limit use of some chemicals, because some chemically treated water may require specialized disposal. Ultraviolet (UV) radiation can be effective as a disinfecting agent, but generally does not help with hyper-concentration and deposition of water borne solids.

High pressure fracturing of rock formations surrounding an oil and/or gas well, typically referred to as fracking, is a water-intensive process. In a fracking process, a mixture of water, sand, and chemicals is injected in a well at high pressures. During the fracking process the pressure is increased until the rock formation surrounding the well fractures and releases the oil and/or gas from the rock, so that they can flow into the well. The fracking waters may contain biological materials, organic materials, inorganic materials or mixtures thereof. The materials may need to be removed from the fracking water to render the water safe for deposal and/or future use. In some instances, the water used to make-up the fracking mixture may need to be treated to remove biological and/or chemicals (such as organic and/or materials) that could contaminant and/or render the fracking mixture unsuitable for the fracking process.

Agriculture waters can include irrigation waters and waters consumed by animals. The agriculture waters can be treated before or after the irrigation process. Animal production facilities, such as but not limited to feedlot facilities, can be a source of water contamination. Feedlot waters can have unsafe levels of nitrates, *Samonella*, *E. Coli*, *Cryptosporidium*, fecal coliform and mixtures thereof.

SUMMARY

Embodiments of the present disclosure are directed to solving these and other problems and overcoming the disadvantages of the prior art. More particularly, embodiments of the disclosed systems and methods provide for the maintenance and/or improvement of water quality. As examples, and without limitation, embodiments of the present disclosure can be applied in connection with maintaining the quality of water in cooling towers, evaporative coolers, heat exchangers, chillers, process recirculation systems, swimming pools, fountains or other architectural water features, agricultural waters, such as feedlot and irrigation waters, recreational waters, hydraulic fracturing waters, waters associated with oil and gas production, flowback waters, wastewater treatment systems, and the like. Treatment systems and methods as disclosed herein utilize ultraviolet (UV) radiation or light. Embodiments can additionally utilize magnetic fields. The UV radiation and/or magnetic fields can be applied directly to water, in order to treat that water. Alternatively or in addition, the UV radiation and/or magnetic fields can be applied to a gas, such as air, and the treated gas can then be placed in contact with water, in order to treat the water.

In accordance with exemplary embodiments of the present disclosure, the UV radiation can comprise ultraviolet radiation having multiple wavelengths. For example, UV radiation at wavelengths of about 180 nm and about 254 nm can be utilized. Magnets can be provided as part of linear arrays. Moreover, such linear arrays can be arranged in pairs. As an example, a pair of linear arrays of magnets can be located adjacent a UV lamp within a treatment chamber, in order to treat a gas contained within the treatment chamber with UV radiation and a magnetic field simultaneously.

In accordance with at least some embodiments a gas is treated with UV radiation and the treated gas is then placed in contact with water. A pump can be provided to supply pressurized air to a treatment chamber containing a UV light source. The treatment chamber can additionally include linear arrays of magnets. Pressurized gas exposed to the UV radiation and, if magnets are provided, a magnetic field, then exits the treatment chamber and is placed in contact with the water to be treated.

Embodiments of the present disclosure are related to systems for treating water. Such systems can include a treatment chamber housing that defines an interior volume. A treatment chamber inlet is operable to admit air into the interior volume of the treatment chamber housing. Located within the treatment chamber housing is a UV radiation source. A treatment chamber outlet is provided that is operable to exhaust air from the interior volume of the treatment chamber housing.

Systems can include additional elements, alone or in combination. Such elements include, for example, an air pump, wherein an outlet of the air pump provides a flow of air to the treatment chamber inlet. The UV radiation source can be operable to emit ultraviolet radiation at a plurality of wavelengths, including radiation having a first wavelength that is within a range of from about 178 nm to about 187 nm, and including light at a second wavelength that is within a range from about 252 nm to about 256 nm. The system can further include a plurality of UV radiation sources within the interior volume of the treatment chamber housing. A plurality of magnets can be included within the interior of the treatment chamber. The magnets can be arrayed along at least a first line, forming a linear array, wherein the polarity of the magnets arrayed along the first line are such that a first magnet in the line repels a second magnet in the line. In accordance with still further embodiments, the magnets can be arrayed along at least first and second lines, wherein the polarity of the magnets arrayed along the first line are such that a first magnetic repels a second magnet in the first line, wherein the polarity of the magnets arrayed along the second line are such that a first magnet repels a second magnet in the second line, wherein the first magnet of the first line is adjacent the first magnet of the second line, wherein the second magnet of the first line is adjacent the second magnet of the second line, and wherein the first adjacent magnets and the second adjacent magnets have magnetic fields or polarities that are oppositely aligned.

Other embodiments provide systems for treating water that can include an air pump. In addition, the systems can include a first treatment chamber having a treatment chamber housing that defines an interior volume or a first treatment volume, and an inlet to the interior volume, wherein the inlet is interconnected to an outlet of the air pump by at least a first supply tube or conduit. The systems can further include an outlet from the interior volume. In addition, a UV light source is located within the interior volume of the first treatment chamber.

Systems can additionally include other elements alone or in combination. For instance, a system can include a second treatment chamber. The second treatment chamber can have a treatment chamber housing, wherein the treatment chamber housing defines an interior volume or treatment volume of the second treatment chamber, an inlet to the interior volume, wherein the inlet is interconnected to an outlet of the air pump by at least a second supply tube or conduit, and an outlet from the interior volume. A second UV radiation source is located within the interior volume of the second treatment chamber. In addition, a common outlet, wherein the outlet from the interior volume of the first treatment chamber and the outlet from the interior volume of the second treatment chamber are interconnected to the common outlet, can also be provided. The first treatment chamber can further include a first plurality of magnets arranged along a first line, wherein an orientation of magnets within the first plurality of magnets alternates. The first treatment chamber can additionally include a second plurality of magnets arranged along a second line, wherein an orientation of the magnetic poles of magnets within the second plurality of magnets alternates, and wherein an orientation of the magnetic poles of each magnet in the first plurality of magnets is reversed from an adjacent magnet in the second plurality of magnets. Similarly, the second treatment chamber can include a third plurality of magnets arranged along a third line, wherein an orientation of the magnetic poles of magnets within the third plurality of magnets alternates, and a fourth plurality of magnets arranged a fourth line, wherein an orientation of magnets within the fourth plurality of magnets alternates, and wherein an orientation of the magnetic poles of each magnet in the third plurality of magnets is reversed from an adjacent magnet in the fourth plurality of magnets.

The methods disclosed herein can further include methods for treating water that comprise contacting an oxygen-containing gas stream with ultraviolet radiation to form treated oxygen gas and, thereafter, contacting a water stream with the treated gas to form a treated water stream. Additional aspects of methods in accordance with the present disclosure can include contacting the oxygen containing gas stream with the ultraviolet radiation within a magnetic field. The magnetic field can be established between two parallel sets of magnets with alternating magnetic poles. The oxygen-containing gas stream can comprise air. Moreover, contacting the oxygen containing gas stream with ultraviolet radiation can be performed at a pressure greater than ambient pressure, preferably from about 55 inches to about 4,000 inches of water greater than ambient atmospheric pressure. The ultraviolet radiation can include wavelengths of at least about 180 nm and about 254 nm. The ultraviolet radiation can comprise substantially ultraviolet radiation of about 180 nm and about 254 nm wavelengths. Contacting the water stream with the treated oxygen gas stream can include at least one of: forming a dispersion of the treated oxygen gas in the water stream; bubbling the treated oxygen gas into the water stream; and introducing the treated oxygen gas through a venturi effect to the water stream. Moreover, the water stream can be substantially free of one or both of free chlorine and chlorine disinfection byproducts. The method can additionally include contacting a calcium containing deposit with the treated water stream to remove at least some of the calcium containing deposit and to form a calcium-laden water. Preferably, the treated water stream has a cycle of concentration more than about 1, more preferably a cycle of concentration more than about 4. The contacting of the oxygen containing gas stream with the ultraviolet radiation can be substantially at ambient temperature and at a pressure of no less than about 55 inches of water and no more than about 4,000 inches of water above ambient atmospheric pressure, and wherein the treated water contains less than about 50,000 colonies of bacteria per mL.

Additional features and advantages of embodiments of the present disclosure will become more readily apparent from the following description, particularly when taken together with the accompanying drawings.

DETAILED DESCRIPTION

Figure 1:
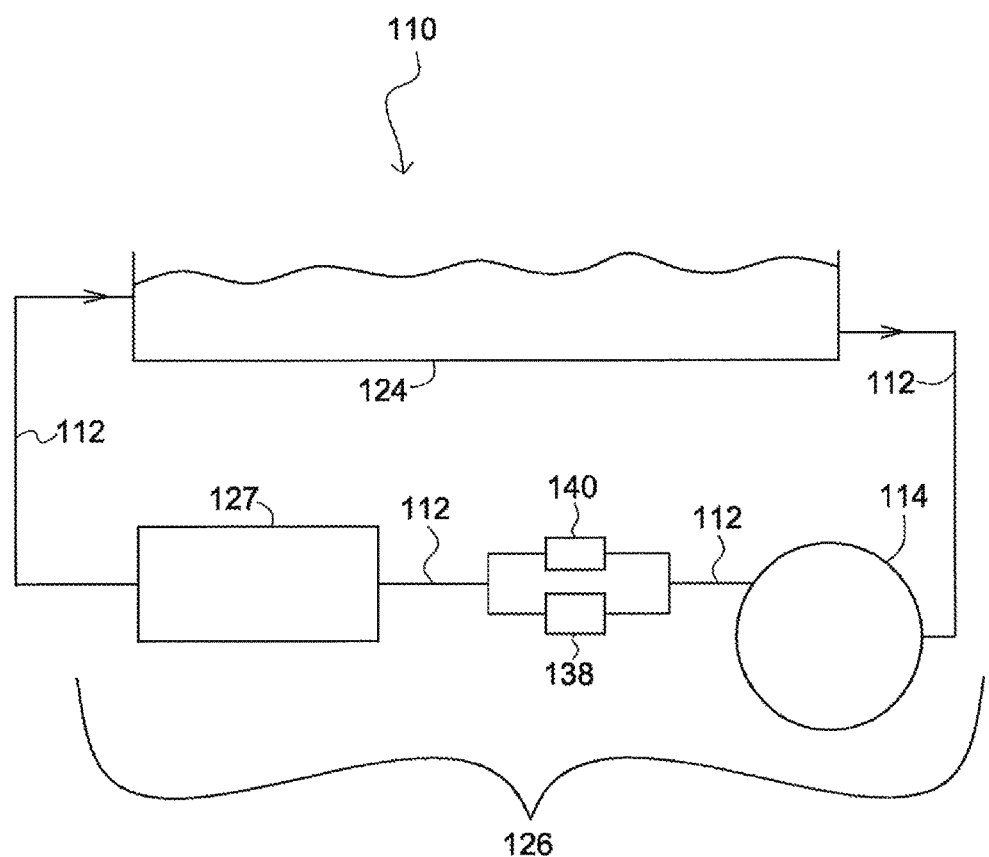
FIG. 1 is a schematic view of a water treatment device according to one embodiment of the present invention.

Embodiments of the present invention comprise water treatment devices that utilize UV radiation, a magnetic field, and/or ozone fortified air to treat solute-laden water, highly alkaline water, and biologically contaminated water, or water that will likely become highly alkaline or biologically contaminated in the absence of treatment. The biologically contaminated water may include a bacterium or chemical contaminate having biological activity. Non-limiting examples of chemical contaminates having biological activity are nitrates, uranium, sulfates, and arsenic to name a few. Examples of water that can be treated using systems or methods as described herein include, but are not limited to, oil or gas well by-product water and other contaminated water generated as a by-product of an industrial process or processes. Embodiments of the present invention are also effective at treating swimming pool water and spa or hot tub water, where the water treatment devices typically reduces or eliminates the need for chlorine in the water. Furthermore, embodiments of the present invention are also effective at treating water associated with petroleum and gas production systems, hydraulic fracturing waters (use in petroleum and gas producing industries), waters associated with petroleum and gas production (including waters co-produced with petroleum and/or gas, injection waters associated with primary, secondary and tertiary petroleum and/or gas produce, and disposal of co-produced waters), feedlot waters, architectural waters, agricultural waters, recreational waters, flowback waters, and various wastewater treatment systems.

By use of the water treatment device, the pH of solute laden water such as cooling tower water is modulated, and biological contamination is highly controlled without the use of, or with substantially reduced use of, chemical agents. Water treatment costs are therefore reduced by use of the water treatment device over chemical treatment alone. Embodiments of the present invention effectively treat cooling tower water by preventing or eliminating biological contamination of the water, and by lowering pH about 0.2 units, or maintaining cooling tower water pH 0.2 units below what the pH would be if the cooling tower water were untreated.

Embodiments of the water treatment device disclosed herein can mitigate total alkalinity such that alkalinity does not concentrate as fast as calcium ions, water hardness, chloride ions, conductivity, or other indices of cycles of concentration. In a typical installation, total alkalinity is 50%-75% of expected alkalinity based on cycles of concentration indicated by an increase in chloride ion concentration. The reduced alkalinity can be highly beneficial, with deposition of scale and other mineral deposits on cooling tower parts being greatly reduced or eliminated completely.

Embodiments of the water treatment device disclosed herein can modulate and/or break the surface tension of water. In agricultural applications, this modulation and/or breaking of the surface tension can increase the solubility of the water in soil. This results in both a faster and greater absorption of the water; hence reduces evaporation and overall water demand.

Embodiment of the water treatment device disclosed herein can reduce bacteria and Leginonella populations in water. While not wanting to be limited by example the water treatment device can reduce the average free-floating Heterotrophic Plate Count (HPC) bacteria, Legionella growth or both in water. For example, the average free-floating HPC bacteria concentration can be commonly reduced by more than about 90%, more commonly by more than about 95%, even more commonly by more than about 98%, yet even more commonly by more than about 99%, or still yet even more commonly by more than about 99.9%. Water treated by the water treatment device disclosed herein can met the generally accepted industrial bio-fouling control recommendation for free floating bacteria. Moreover, the water treatment device can commonly achieve at least about 70% reduction in concentration of immobile HPC bacteria, more commonly about 75% reduction in concentration of immobile HPC bacteria, even more commonly about 80% reduction in concentration of immobile HPC bacteria, yet even more commonly about 85% reduction in concentration of immobile HPC bacteria, or still yet even more commonly about 90% reduction in concentration of immobile HPC bacteria. Waters treated by the water treatment device typically have a reduction in free-floating *Legionella* concentrations of about at least 60%, more typically a reduction in free-floating *Legionella* concentrations of about at least 65%, even more typically a reduction in free-floating *Legionella* concentrations of about at least 70%, yet even more typically a reduction in free-floating *Legionella* concentrations of about at least 75%, still yet even more typically a reduction in free-floating *Legionella* concentrations of about at least 80%, or yet still even more typically a reduction in free-floating *Legionella* concentrations of about at least 85%.

Feedlot waters treated by the water treatment device disclosed herein can reduce bacteria colonies compared to untreated waters. While not wanting to limited by example, Coliform levels in feedlot waters can be commonly reduced by a factor of about 1,000, more commonly by a factor of about 5,000, or even more commonly by a factor of about 10,000. For water treated with the water treatment disclosed herein, the HPC levels of feedlot waters can be typically reduced by a factor of at least 25, more typically by a factor of about 50, or more typically of about 100 compared to untreated waters. Moreover, levels of *Staphylococcus Aureus* (Staph) in feedlot waters can be commonly reduced by the water treatment device disclosed herein by about a factor of about 2, more commonly by a factor of about 5, or even more commonly by a factor of about 10. Furthermore, *Escherichia Coli* (*E. Coli*) levels in feedlot waters can be commonly reduced by the water treatment device disclosed herein by about a factor of about ¼, more commonly by a factor of about ⅓, or even more commonly by a factor of about ½. The water treatment device can nearly eradicate *Listeria* in feedlot waters.

Embodiments of the water treatment device disclosed herein can operate to increase calcium concentration where the water treatment device is installed on a cooling water system that has incurred substantial mineral deposits. In many cases, the substantial mineral deposits can be substantially or completely eliminated. The substantial mineral deposits are typically eliminated within a year of installing the water treatment device.

In some embodiments, the water treatment device includes a glass media filter. The filter can remove or reduce suspended solids, including dead bacteria, and may help prevent infestation of water with *Legionella* bacteria.

Embodiments of the water treatment device disclosed herein can include the water treatment device interconnected up-stream, down-stream and/or in parallel with one or more of a cavitation device, reverse osmosis device, a filtration device and flocculation system.

Terminology

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning "either or both."

References in the specification to "one embodiment", "an embodiment", "another embodiment, "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "couple" or "coupled" as used in this specification and appended claims refers to an indirect or direct connection between the identified elements, components, or objects. Often the manner of the coupling will be related specifically to the manner in which the two coupled elements interact.

The term "approximately," as used in this specification and appended claims, refers to plus or minus 10% of the value given. For example: "approximately 14.0 watts" means a range from 12.6 watts to 15.4 watts.

The term "about," as used in this specification and appended claims, refers to plus or minus 20% of the value given.

The terms "hyper-concentrated," and "solute laden," as used in this specification and appended claims, refers to circulating water (cooling tower water) that contains dissolved solids and other dissolved species at concentrations that are elevated at least 2 fold over feed water. For example, circulating water at a cycle of concentration of 2 is hyper-concentrated with dissolved solids.

The terms "biologically contaminated" and "biologically contaminated water," as used in this specification and appended claims, generally refers to water containing bacterial matter and, thereby, generally rendering the water unsuitable for its intended purpose. The terms "Heterotrophic Plate Count" or "HPC" generally include bacteria such as: species within the genera *Pseudomonas, Aeromonas, Alcaligenes, Acinetobacter, Klebsiella, Flavobacterium, Chromobacterium*, and others. The HPC bacteria are considered to be opportunistic pathogens for mammals. Moreover, the HPC bacteria can cause disease in healthy, as well as, immune compromised mammals. The terms "polluted" or "polluted water" refers to water that is unfit or undesirable for its intended use. Thus water that is intended to be used as drinking water may be polluted, but that same water could be acceptable, and therefore not polluted, if intended to be discharged into a river.

The term "oxygenated gas," as used in this specification and appended claims, refers to a gas phase mixture or solution comprising some form of oxygen at a level of at least 1% by weight. Forms of oxygen include monoatomic oxygen (O); diatomic oxygen, also known as ground state (triplet, $3\Sigma_g^-O_2$) molecular oxygen ($O_2$); ozone or triatomic oxygen ($O_3$); diatomic oxygen with electrons in either of two excited states ($^1\Delta_g^-O_2$ and $^1\Sigma_gO_2$) known as singlet oxygen (either form of singlet oxygen represented here as $^1O_2$); and superoxide anion ($O_2^-$).

The term "air," as used in this specification and appended claims, refers to the commonly recognized gas that surrounds the surface of the earth and comprises approximately 78.08% $N_2$, 20.95% $O_2$, 0.934% Ar, and 0.0383% $CO_2$ by volume using the 1976 Standard Atmosphere values at sea level.

The term "oxygen supplemented air," as used in this specification and appended claims, refers to air comprising greater than 21.1% $O_2$ by weight.

The term "ozone fortified gas," as used in this specification and appended claims, refers to a gas comprising greater than 600 parts per billion ozone.

The term "ozone fortified air," as used in this specification and appended claims, refers to air comprising greater than 600 parts per billion ozone.

The term "ultraviolet radiation" or "UV radiation," as used in this specification and appended claims, refers to electromagnetic radiation having wavelength in a range from 40 nm to 400 nm. Accordingly, a UV radiation source emits electromagnetic radiation having wavelength in a range from 40 nm to 400 nm.

The term "substantially UV transmissive" or "substantially UV transmissive material," as used in this specification and appended claims, refers to material that transmits 50% or more of radiation having a wavelength of about 180 nm and/or about 254 nm, per 1 mm of material.

The term "substantially parallel," as used in this specification and appended claims, refers to lines or axes are relative to one another plus or minus 3°.

Embodiments of Water Treatment Devices

A first embodiment water treatment device 126 is illustrated in FIGS. 1-4; none of FIGS. 1-4 are drawn to scale. A schematic representation of the first embodiment water treatment device 126 installed in a water re-circulating system 110 is illustrated in FIG. 1. Non-limiting example of such water re-circulating systems are cooling tower water systems, swimming pool or spa systems, architectural systems, agricultural systems and such. The first embodiment water treatment device 126 comprises a radiation chamber 127, a gas injector 138, a valve 140, and a pump 114. The gas injector 138 of the first embodiment water treatment device is a venturi. The water re-circulating system 110 further comprises conduit 112 and a reservoir 124. The conduit 112 serves to conduct water between the reservoir 124 and the water treatment device 126, as well as to conduct water within the water treatment device 126. The reservoir 124 of the water re-circulating system 110 is, for example, a cooling tower basin, the cooling tower of which is paired to an air conditioner. A water treatment flow path proceeds clockwise from the reservoir 124 to the pump 114, then to either the valve 140 or the gas injector 138, before entering the radiation chamber 127 and finally returning to the reservoir 124. The water treatment flow path includes conduit 112 that travels between or through the other components disclosed above.

In operation, as illustrated in FIG. 1, water typically flows in a clockwise direction from the reservoir 124 to the pump 114, then to the gas injector 138. The reservoir serves as both a source of tainted water to be treated by the water treatment device 126 and as a destination for treated water.

In some embodiments, treated water does not return to the source of the tainted water. For example, when used in connection with petroleum and gas production systems, feedlot systems, agricultural systems or the like, water received from the system may be treated and then placed in a storage reservoir or passed to another system for further use and/or recycling.

In typical operation of the water treatment device 126, water flows through either the gas injector 138 or valve 140 before entering the radiation chamber 127. The gas injector (venturi) injects oxygenated gas into water that flows therethrough. Examples of oxygenated gas include, but are not limited to, air, oxygen supplemented air, relatively pure oxygen, ozone fortified air, and ozone fortified gas. Alternatively, water may flow through the valve 140, with volumes and proportions of water flowing through either the valve or the gas injector varying inversely, and water flow through the venturi thus being modulated by use of the valve. As is apparent to a person of ordinary skill in the art flow of water through the venturi is generally increased by closing or partially closing the valve. In some embodiments, the valve 140 is absent, and the proportion of water flow through the gas injector 138 is adjustable primarily through adjusting the flow rate of the pump 114. In some embodiments, the gas injector 138 is supplemented or supplanted by gas injection means other than the venturi. Gas injection means are adapted to inject gas into the flowing water, and include, but are not limited to, gas jets or nozzles adapted to inject gas under positive pressure into the water.

Water flows into the radiation chamber 127 where it is typically irradiated with UV radiation and subjected to a magnetic field. Treated water emerges from the radiation chamber whereupon it flows back to the reservoir 124. The radiation chamber 127 of the water treatment device 126 is illustrated in detail in a cross-section view in FIG. 2. The gas injector 138, which is a venturi, is also shown in greater detail in FIG. 2. The radiation chamber comprises a four inch diameter, thirty eight inch long UV resistant acrylonitrile butadiene styrene (ABS) plastic enclosure 128, within which is housed a UV radiation source 130, a magnetic rod 132, and a flow cell 142. The radiation chamber further comprises a bracket 154 in which is disposed an orifice 150 through which gas is relatively free to pass.

The magnetic rod 132 of the first embodiment is a tube within which resides permanent magnets 134. The tube can comprise a polymeric material or non-magnetic metal. Non-limiting examples of polymeric materials include thermoplastic organic polymers, thermosetting organic polymers and combinations thereof. Non-limiting examples on non-magnetic metals include copper and its alloys (such as brass) and aluminum to name a few. The number of magnets can vary depending on the size of water treatment device. While not wanting to be limited by example, the number of permanent magnets per tube commonly can be from about 4 to about 12 or more commonly from about 6 to about 10. In some examples the number of magnets per tube is typically six, more typically about eight and yet more typically about ten. Other embodiments may use electromagnets in place of or in addition to permanent magnets.

The flow cell of the first embodiment water treatment device is a glass tube having an inside diameter of one inch and comprising UV quality quartz glass. The UV quality quartz glass of the first embodiment is GE Type 214 fused quartz (Momentive Performance Materials Quartz, Inc., Strongsville, Ohio), having UV radiation transmission of approximately 70% (per 1 mm material) at 180 nm and UV radiation transmission greater than 85% (per 1 mm material) at 254 nm. Other embodiments of water treatment devices include flow cells comprising substantially UV transmissive material. The flow cell 142 has a flow cell length 143 residing along a flow cell axis of cylinder, the flow cell length being approximately 30 inches. In other embodiments, the flow cell length is preferably at least 10 inches, more preferably at least 20 inches, and most preferably at least 30 inches. The flow cell is best adapted to irradiation along its flow cell length.

The UV radiation source 130 can be any UV source providing one or both of 254 and 180 nm light. An example of a suitable UV radiation source 130 is a G36T5VH/4P (manufactured by USHIO America, Inc., a subsidiary of USHIO Inc. of Japan) ozone producing quartz UV lamp operating at approximately forty (40) watts power consumption, with a main spectral peak at approximately 253.7 nm and another spectral peak at approximately 180 nm. The G36T5VH/4P ozone producing quartz UV lamp is generally elongate and cylindrical, having a length of about 33 inches and a diameter of about 0.6 inches. It uses a universal B224PWUV-C ballast. The G36T5VH/4P lamp consumes approximately forty (40) watts power and emits approximately fourteen (14) watts power in the form of ultraviolet radiation. As is known to persons of ordinary skill in the art, radiation having a wavelength around 254 nm is highly antimicrobial. Another example of a suitable UV radiation source 130 is sunlight. Similarly, radiation having a wavelength around 180 nm generates ozone in air, albeit inefficiently relative to corona discharge.

The flow cell 142 is coupled to the conduit 112 at conduit junctions 113, and cooling tower water flows through it during water treatment. Relatively high UV transparency of the quartz glass flow cell allows UV radiation to penetrate the flow cell to irradiate water contained therein. In the first embodiment, a distance between the UV radiation source and the flow cell is approximately 0.50 inch. In other embodiments, a distance between the UV radiation source and the flow cell is preferably between 0.1 and 12 inches, more preferably between 0.2 and 6 inches, and most preferably between 0.40 and 2.0 inches.

The magnets 134 of the magnetic rod 132 are cylindrically shaped neodymium (Neodymium-Iron-Boron) grade N52, each magnet having a cylinder diameter of approximately 0.50 inch and a cylinder height of approximately 0.50 inch. The magnets are disposed in copper tubing having an inside diameter of approximately 0.50 inch, and are arranged with like poles of adjacent magnets oriented toward each other, as illustrated in FIG. 4. In the first embodiment, a distance between the magnetic rod and the flow cell is approximately 0.50 inch. In other embodiments, a distance between the magnetic rod and the flow cell is preferably between 0.1 and 12 inches, more preferably between 0.20 and 6 inches, and most preferably between 0.40 and 2.0 inches. In some embodiments, weaker permanent magnets are used. Electromagnets may also be used.

Figure 2:
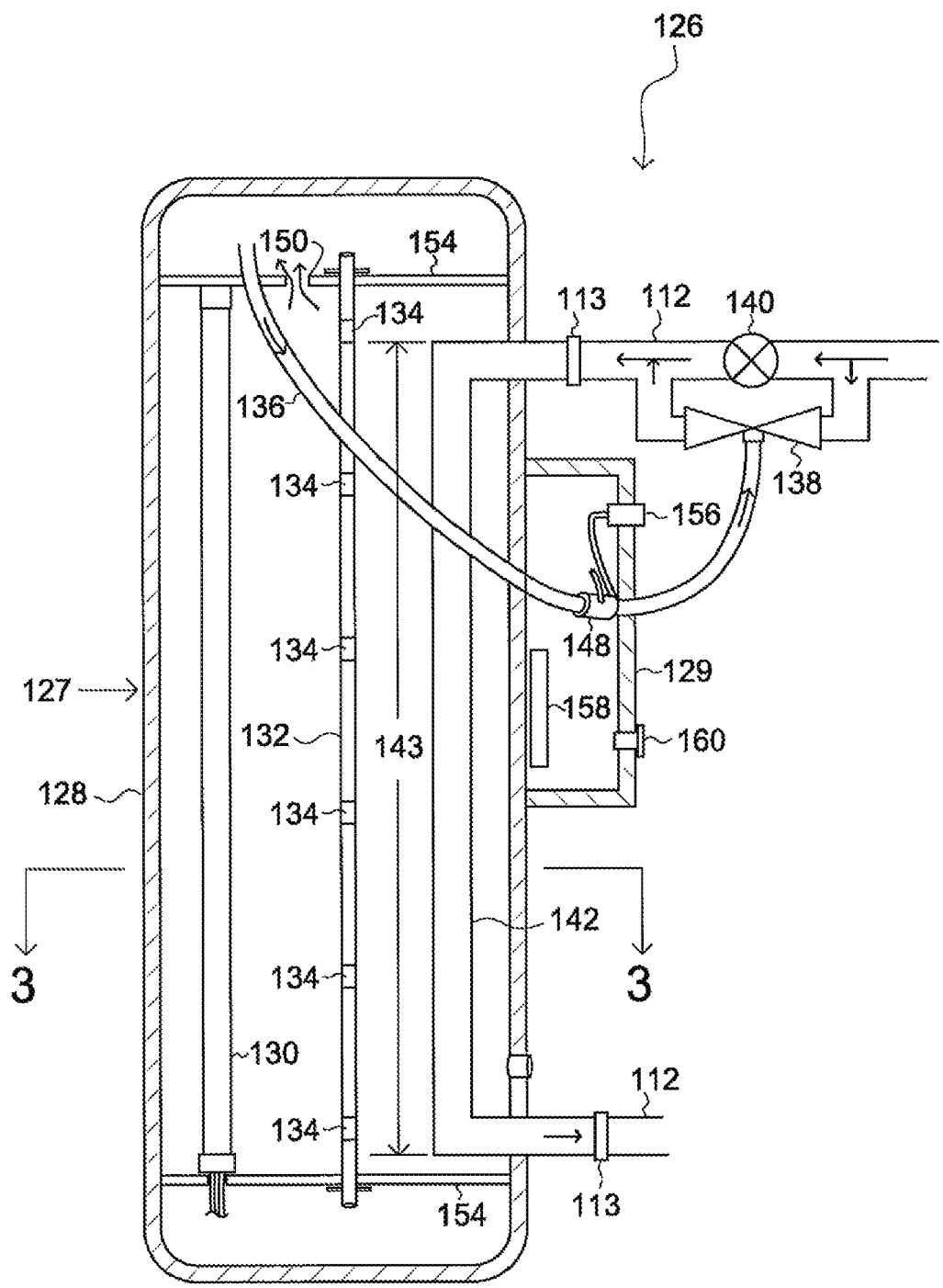
FIG. 2 is a side cross-section view of a water treatment device according to one embodiment of the present invention.

The first embodiment radiation chamber actually comprises two UV radiation sources (G36T5VH/4P ozone producing quartz UV lamps), two magnetic rods, and a single flow cell. In order to provide a simpler, less cluttered figure, only one UV radiation source 130 and one magnetic rod 132 are illustrated in FIG. 2. Similarly, as illustrated in FIG. 2, the magnetic rod 132 appears closer to the flow cell than does the UV radiation source. Orientation of the two UV radiation sources 130, two magnetic rods 132, and flow cell 142 inside the housing 128 of the radiation chamber 126 of the first embodiment water treatment device is better illustrated in FIG. 3, which illustrates a radial cross section of the radiation chamber.

Each of the flow cell 142, the UV radiation source 130, and the magnetic rod 132 are generally cylindrical, which means that each of the flow cell, UV radiation source, and magnetic rod have an axis of cylinder. As best illustrated in FIG. 2, the axes of cylinder for each of the flow cell, UV radiation source, and magnetic rod, are substantially parallel.

Radiation chambers typically comprise two G36T5VH/4P UV lamps, two magnetic rods, and a single one inch inside diameter flow cell, contained within an ABS plastic housing. A water treatment device comprising the single radiation chamber described above and a Mazzei #748 venturi drawing one cubic foot per hour (CFH) ozone fortified air from within the radiation chamber is sufficient to effectively treat cooling tower water for up to 1000 tons of refrigeration, even where feed water quality is low. Low quality feed water typically has a pH value of 8.0 or greater and a hardness value of 200 ppm or greater. Additional radiation chambers can be added to increase capacity.

Water flow rate through the gas injector (venturi) 138 and flow cell 142 is typically about ten to twenty gallons per minute (GPM), which facilitates the venture drawing a vacuum of about 15.0 inches Hg to about 25.0 inches Hg. Other embodiments comprise other UV radiation sources and magnets, and can operate effectively at other water flow rates. UV radiation intensity and magnetic field strength in the flow cell impact the maximum water flow rate at which embodiments of the invention can treat water effectively. More powerful or more numerous magnets, or more UV radiation, allow embodiments of the water treatment device to operate effectively at higher water flow rates, or to treat "harder" water. Flow cell configuration can also be adapted to modulate exposure of flow cell contents to UV radiation. Accordingly, configuring the flow cell to increase flow cell contents exposure to UV radiation enables greater water flow rates for a UV radiation source of a given intensity. Similarly, decreasing distance between UV radiation sources and flow cells, or between magnets and flow cells, can result in higher flow rates that still result in effective water treatment.

The gas injector 138 of the first embodiment water treatment device is coupled to a gas feed tube 136, the gas feed tube being adapted to deliver air from inside the radiation chamber 127 to the gas injector, the radiation chamber air being introduced into water flowing at the gas injector. Because air in the radiation chamber is irradiated at about 180 nm, ozone is produced in the radiation chamber air. Thus, radiation chamber air that is introduced into flowing water at the gas injector is ozone fortified.

The gas injector 138 of the first embodiment water treatment device is a Mazzei #748 venturi, which creates air flow of one cubic foot per hour (CFH) when generating a vacuum of 15 inches Hg. In order to operate properly, the venturi of the first embodiment water treatment device draws a minimum vacuum of twelve inches Hg.

The first embodiment water treatment device further comprises a control panel 129 that houses (i) a ballast 158 (Universal # B224PWUV-C) to energize the UV lamp, (ii) a vacuum gauge 156, (iii) a vacuum test valve 148, and, (iv) a UV lamp ON/OFF switch 160.

Figure 3:
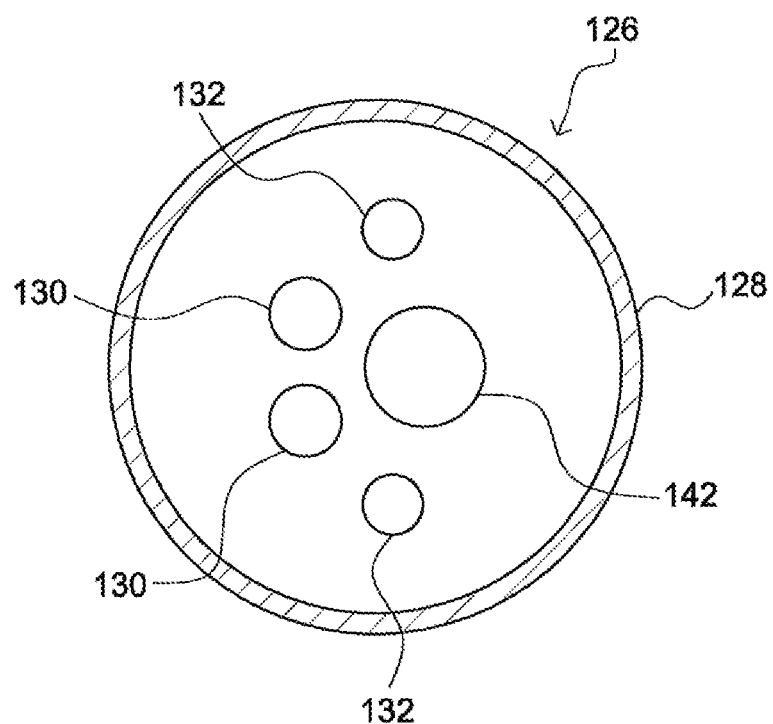
FIG. 3 is a top cross-section view of a water treatment device according to one embodiment of the present invention.

A typical orientation of two UV lamps 130 and two magnetic rods 132 containing a linear array of magnets (not shown) is illustrated in FIG. 3. The orientation of four individual magnets 134 in two adjacent tubes 132 is illustrated in FIG. 4. As an example, the magnets 134 can comprise permanent magnets, such as neodymium magnets. The tube 132 can comprise various materials, such as copper, poly-vinyl-chloride, or other materials.

Figure 4A:
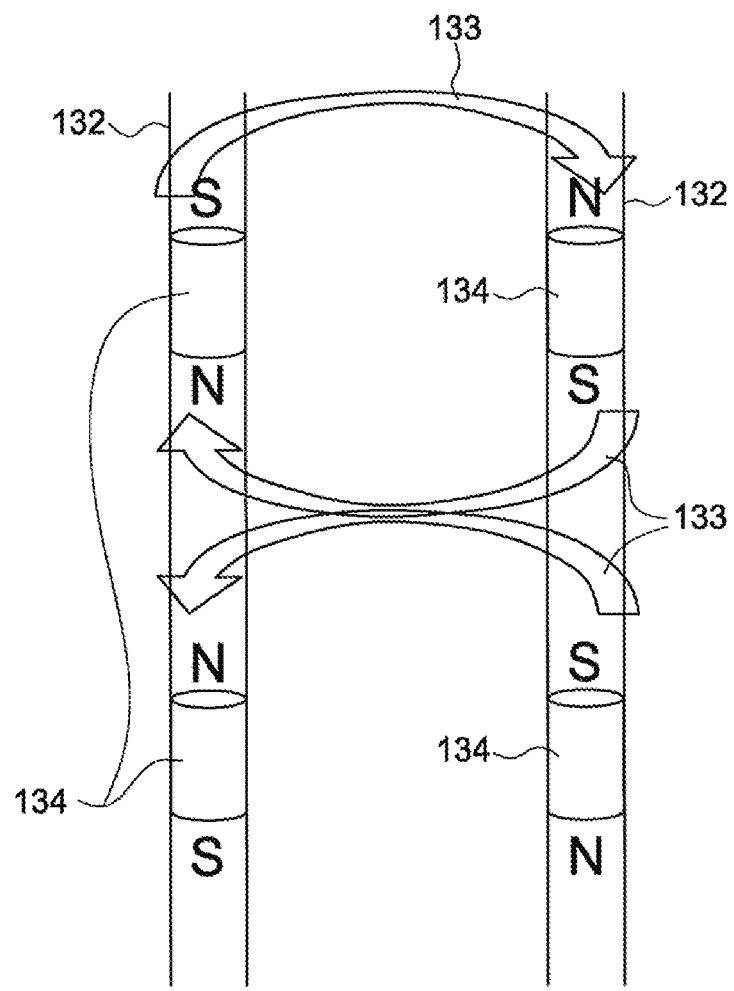
FIGS. 4A-4C are side views of water treatment devices according to various embodiments of the present invention.
Figure 4B:
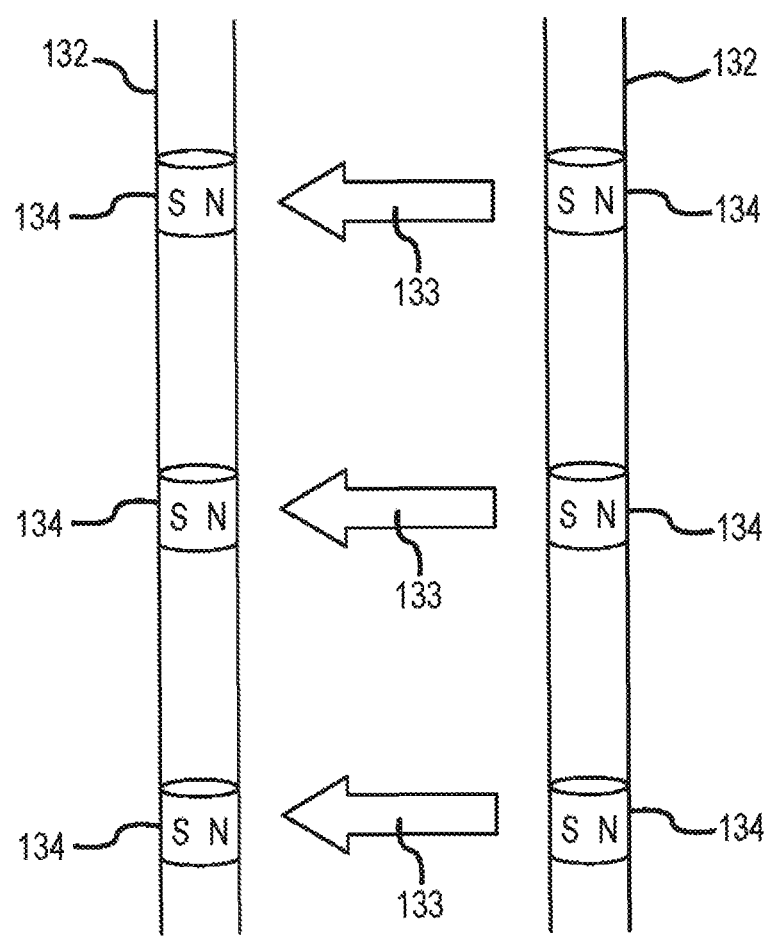
Figure 4C:
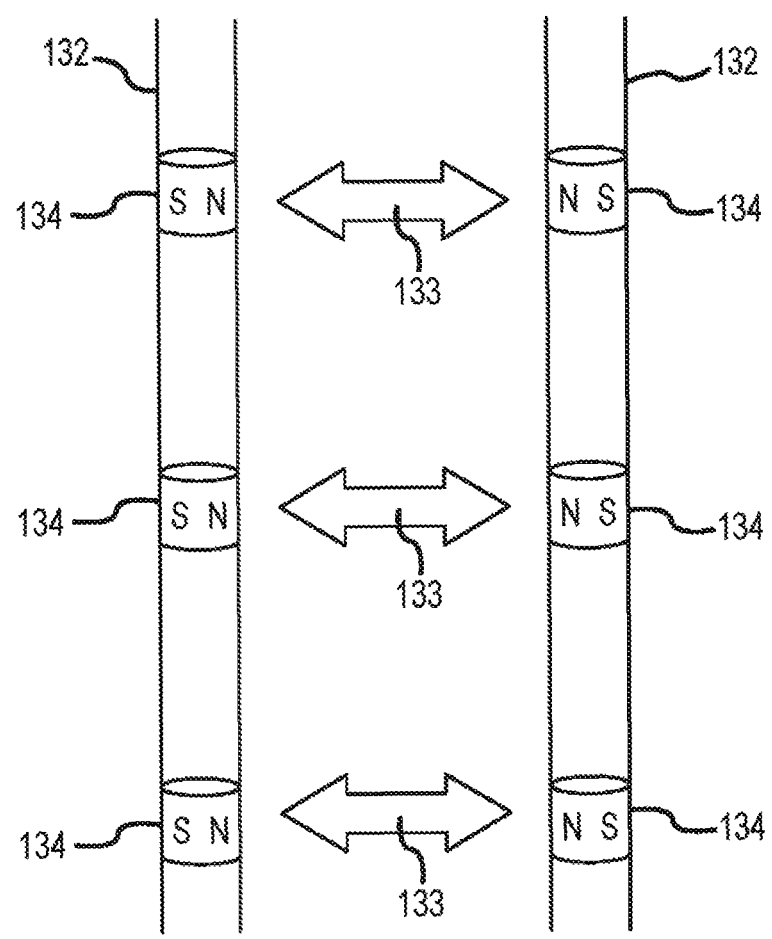

The magnets can be oriented in the tubes in various differing configurations. FIG. 4A depicts the adjacent magnets within one tube oriented with like poles closest to each other. In addition, a first magnet 134 of a first line or linear array of magnets 134 in the first rod 132 is aligned oppositely from a first magnet 134 of a second line or linear array of magnets 134 in the second rod 132. This orientation generates desirable magnetic field orientations, indicated by magnetic field arrows 233. FIG. 4B depicts the magnets 134 oriented within the first rod 132 with one of the North or South poles of the magnets oriented towards the flow cell 142 and the magnets 134 within the second rod 132 with other of the North or South poles of the magnets oriented towards the flow cell 142. FIG. 4C depicts the magnets 134 oriented in the rods 132 oriented with one of the North or South poles towards the flow cell 142.

Examples of cooling tower water during treatment with embodiments of water treatment devices according to the present invention are shown in Table 1. Each of the water treatment devices whose results are summarized in Table I is substantially similar and comprises: two G36T5VH/4P ozone producing quartz UV lamps; two magnetic rods, each magnetic rod comprising six neodymium grade N52 magnets, each magnet being cylindrical and approximately ½ inch diameter by ½ inch long and installed inside ½ inch inside diameter copper tubes; one flow cell comprising an approximately 1 inch inside diameter quartz glass (GE Type 214 fused quartz) tube approximately 30 inches long; and one Mazzei #748 venturi. The water treatment devices are configured as shown in FIGS. 1-4A, with the UV lamps, magnetic rods, and flow cell enclosed in a radiation chamber housing, and the venturi drawing ozone fortified air from within the radiation chamber. The venturi vacuum is maintained at 15 inches to 25 inches Hg, such that the venturi draws approximately 1.0 CFH gas or more from within the reaction chamber. The magnets are oriented in the magnetic rods as shown in FIG. 4A.

water. As measured, however, alkalinity is actually increased only 2.22 times, approximately 60% of the predicted value. This 40% reduction in alkalinity has beneficial effects of permitting cooling tower water to be run at higher cycles of concentration, while minimizing scale and other deposition of solids on cooling tower components. Less water use and cleaner cooling tower components are thus beneficial consequences of the reduced alkalinity. The mechanism of action for reduced alkalinity is not well understood, but is a consequence of treating cooling tower water with the water treatment device.

Figure 5:
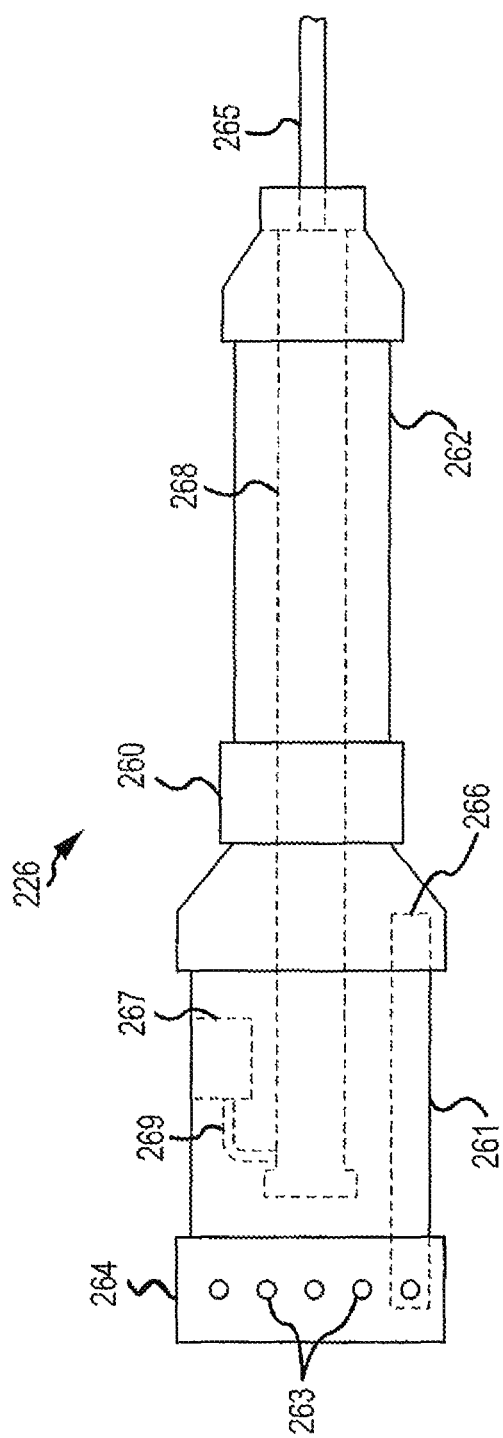
FIG. 5 is a side view of a water treatment device according to one embodiment of the present invention.
Figure 6:
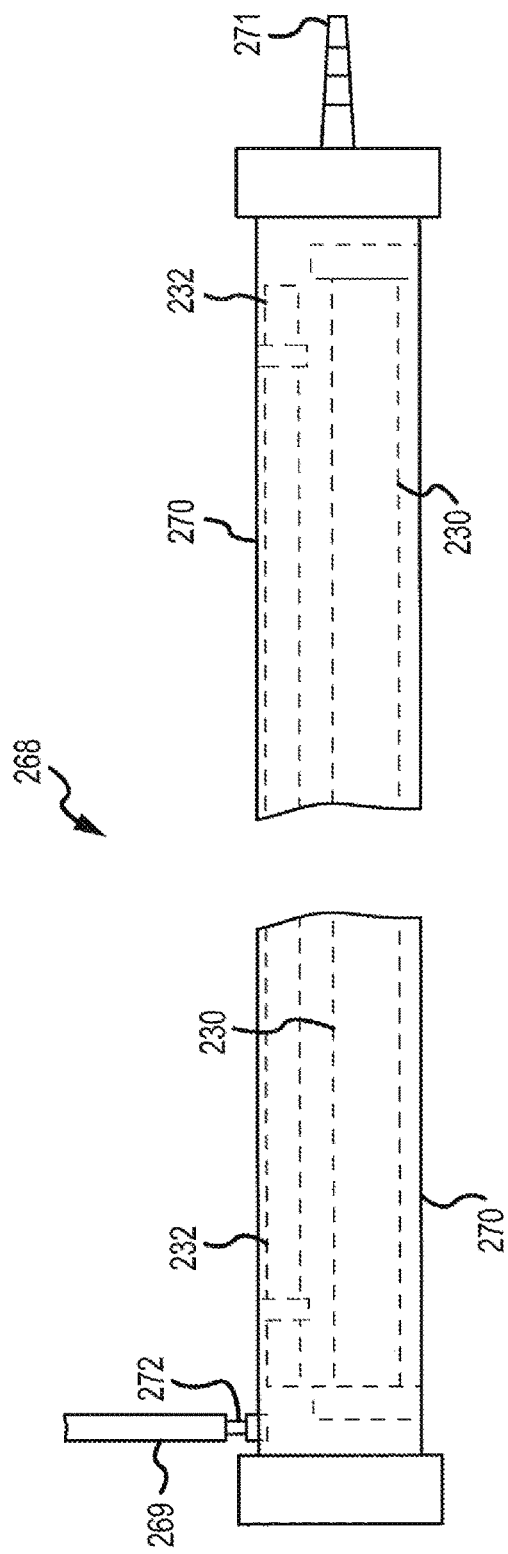
FIG. 6 is a side view of a water treatment device according to one embodiment of the present invention.
Figure 7:
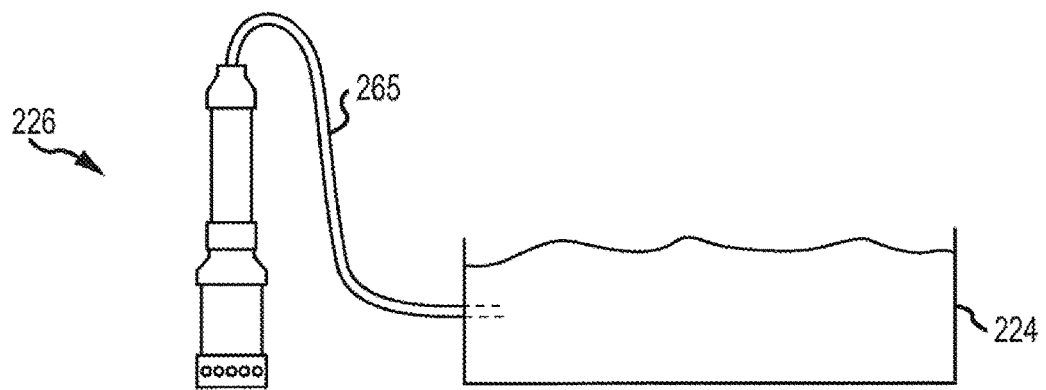
FIG. 7 is a side view of a water treatment device according to one embodiment of the present invention.

A second embodiment water treatment device 226 is illustrated in FIGS. 5, 6 and 7. In its second embodiment, the water treatment device is relatively compact and is adapted to deliver treated gas to a water system. Water typically does not flow through the second embodiment water treatment device. The gas is typically, but not necessarily, an oxygenated gas such as air.

The second embodiment water treatment device 226 comprises a housing 260 within which reside a ballast 266, an electric gas pump 267, and a gas treatment chamber 268. The ballast is a universal B224PWUV-C ballast, and is used to power a UV radiation source (not shown in FIG. 5, shown as element 230 in FIG. 6) that resides in the gas treatment chamber.

The electric gas pump of the second embodiment water treatment device is a Tetra Whisper® 150 aquarium air pump. The electric gas pump delivers air under positive pressure to the gas treatment chamber through a fluid delivery tube 269 at a flow rate of at least 28 liters per hour (L/hr). Flow rates of 300 L/hr or greater may be required for

TABLE I

| FACILITY[A] | SAMPLE[B] SOURCE | COND.[C] | CHLORIDE (ppm) | C of C[D] (chloride) | ALK.[E] (ppm) | C of C[F] (ALK.) | % ALK.[G] |
|---|---|---|---|---|---|---|---|
| A - 400 | Feed water | 1054 | 90 | — | 90 | — | — |
| TONS | Tower water | 4110 | 330 | 3.66 | 200 | 2.22 | 60% |
| B - 540 | Feed water | 930 | 55 | — | 200 | — | |
| TONS | Tower water | 3129 | 220 | 4.0 | 400 | 2.00 | 50% |
| C - 500 | Feed water | 442 | 54 | — | 100 | | |
| TONS | Tower water | 2207 | 284 | 5.26 | 386 | 3.86 | 73% |
| D - 600 | Feed water | 277 | 29 | — | 84 | | |
| TONS | Tower water | 1870 | 213 | 7.34 | 344 | 4.10 | 56% |
| E - 1300 | Feed water | 281 | 25 | — | 74 | | |
| TONS | Tower water | 1663 | 181 | 7.24 | 360 | 4.86 | 67% |

[A]Facilities A-E are cooling towers located in California and Colorado, the cooling towers serving refrigeration/air conditioning units having cooling capacity listed. One ton of cooling capacity = removal of 12000 BTU per hour.
[B]The source of each sample is either tower water, which is concentrated by evaporation that occurs during normal cooling tower operation, or feed water, which is the source for all water in the cooling tower.
[C]COND. = conductivity in microSiemens. Conductivity is a function of ionic species dissolve in the water.
[D]C of C (chloride) = cycles of concentration as calculated using chloride ion concentration. By definition, cycles of concentration of feed water = one. Cycles of concentration of tower water is calculated by dividing tower water chloride concentration by feed water chloride concentration. Chloride ion concentration is used here to calculate cycles of concentration because chloride ion does not evaporate and is unaffected by the water treatment device.
[E]Alkalinity is reported in ppm (mg/L) CaC03.
[F]C of C (alk.) = cycles of concentration as calculated using alkalinity.
[G]% alkalinity is cycles of concentration as calculated using alkalinity, divided by cycles of concentration using chloride. The cycles of concentration using chloride is used here as an index of actual cycles of concentration of cooling tower water.

As shown in Table I, treatment of tower water with the water treatment device results in less alkalinity than would be predicted based on cycles of concentration calculated using chloride ion. Percent alkalinity ranges from 50% to 73% of predicted, the predicted value being based on cycles of concentration calculated using chloride. For instance, for Facility A, a cooling tower servicing a refrigeration unit having 400 tons of cooling capacity, chloride concentration indicates that tower water is 3.66 times as concentrated as feed water (cycles 0 f concentration based on chloride=3.66). Accordingly, one would expect to find total alkalinity in tower water also increased 3.66 times over feed some applications. A barbed fitting 272 penetrates the chamber housing 270 and allows gas to enter the gas treatment chamber from the fluid delivery tube. A fluid exit port 271 is adapted to allow gas under positive pressure to exit the water treatment device, whereupon treated gas typically flows into water in a water system. Except for the barbed fitting and the fluid exit port, the gas treatment chamber is substantially gas tight.

In some embodiments, the electric gas pump 267 can be augmented and/or replaced with an oxygen concentrator. The oxygen concentrator can be any device that processes ambient air to increase the oxygen content of the air. Two non-limiting example of oxygen concentrators are vacuum swing adsorption and pressure swing adsorption concentrators.

In some embodiments, the gas may one of humidified or de-humidified before entering the gas treatment chamber 268. For example, the gas may de-humidified to have a relative humidity commonly of no more than about 40%, more commonly of no more than about 30%, even more commonly of no more than about 20%, yet even more commonly of no more than about 10%, or still yet even more commonly of no more than about 5%. Or, for example, the gas may be humidified to have a relative humidity typically of more than about 60%, more typically of more than about 70%, even more typically of more than about 80%, yet even more typically of more than about 90%, or still yet even more typically of more than about 95%.

The gas treatment chamber 268 also houses a magnetic rod (not shown in FIG. 5, shown as element 232 in FIG. 6). The housing 260 further comprises gas inlet ports 263 that reside in a removable access cap 264. The water treatment device 226 further comprises a gas outlet tube 265. In typical operation, air is pumped from within the housing, through the gas treatment chamber 268, and out the gas outlet tube 265. As air is removed from the water treatment device by flowing out the gas outlet tube 265, it is replaced by outside air that inters the housing through the gas inlet ports 263.

In accordance with at least some embodiments, the housing 260 is approximately 40 inches long, and comprises a butt portion 261 and an aft portion 262. The housing 260 can be formed from a polyvinyl chloride (PVC) material. In other embodiments, the housing and gas treatment chamber include materials such as, but not limited to, metal, metal alloys, composites, and natural and synthetic polymers. The butt portion 261 can comprise a cylindrical PVC tube approximately 14 inches long and having an inside diameter of approximately six inches. The aft portion 262 can comprise a PVC tube approximately 26 inches long and having an inside diameter of approximately 4 inches.

The gas treatment chamber 268 comprises a chamber housing 270, the chamber housing can include acetonitrile butadiene styrene (ABS) tube approximately 36 inches long with an inside diameter of approximately 1.5 inches. The UV radiation source 230 resides in the gas treatment chamber. As an example, the UV radiation source can comprise a model G36T5VH/4P ozone producing quartz UV lamp from Ushio America, Inc. (Cypress, Calif.). The model G36T5VH/4P lamp operates at approximately forty (40) watts power consumption and has a main spectral peak at approximately 253.7 nm and another spectral peak at approximately 180 nm. The UV lamp is generally elongate and cylindrical, having a length of about 33 inches and a diameter of about 0.6 inches. It consumes approximately forty (40) watts power and emits approximately fourteen (14) watts power in the form of ultraviolet radiation. As is known to persons of ordinary skill in the art, radiation having a wavelength around 254 nm is highly antimicrobial. Similarly, radiation having a wavelength around 180 nm generates ozone in air, albeit inefficiently relative to corona discharge.

One or more magnetic rods 232 also reside within the gas treatment chamber 268. The magnetic rods can comprise a non-magnetic tube within which resides two or more permanent magnets (not shown). The non-magnetic tube may comprise an organic polymeric material or a non-magnetic metallic material. The magnets of the magnetic rod 232 may be cylindrically shaped neodymium (Neodymium-Iron-Boron) grade N52 magnets, each magnet having a cylinder diameter of approximately 0.50 inch and a cylinder height of approximately 0.50 inch. The magnets of the second embodiment are rare earth magnets. Other embodiments use other rare earth magnets such as samarium-cobalt magnets. The non-magnetic tube has an inside diameter of approximately 0.50 inch. The magnets and the one or more magnetic rods 232 may be arranged in any of the arrangements depicted in FIGS. 4A-4C.

Except for the barbed fitting 272 and the fluid exit port 271, the gas treatment chamber is substantially gas tight. Accordingly, air or other gas pumped into the gas treatment chamber through the barbed fitting can only exit the chamber through the fluid exit port. Apertures in the gas treatment chamber through which wires enter the chamber in order to supply electricity to the UV lamp are well sealed in order to maintain a substantially gas tight chamber.

Wiring of electrically powered components such as the ballast, air pump, and UV radiation source is not shown in the figures. However, persons of ordinary skill in the art recognize that the ballast is wired to the UV lamp, and that the water treatment device is electrically coupled to a source of electric power in order to operate. Typical electrical coupling includes, but is not limited to, plugging into an electrical outlet or hard-wiring.

The second embodiment water treatment device 226 is merely exemplary. Other embodiments comprise other UV radiation sources, including, but not limited to, other UV lamps, lasers, or diodes adapted to emit radiation in the ultraviolet range. Some embodiments do not require a ballast, or use a different ballast than the B224PWUV-C. Non-limiting examples of suitable lamps include arc, discharge (including noble gas, sodium vapor, mercury vapor, metal-halide vapor or xenon vapor), induction, plasma, low-pressure, high-pressure, incandescent and discharge lamps emitting ultra-violet radiation having suitable wavelengths. Examples of suitable lasers without limitation, include gas, chemical, excimer, solid-state, fiber, photonic, semi-conductor, dye or free-electron laser operate in one of continuous or pulsed form. Furthermore, suitable diodes include without limitation are diamond, boron nitride, aluminum nitride, aluminum gallium nitride, and aluminum gallium, indium nitride. The water treatment device 262 may or may not be coated on the inside with a UV reflective coating. Moreover, the water treatment device 262 may be configured to focus the UV radiation emitted from the UV radiation source on the gas treatment chamber 268. For example, the water treatment device 262 can have a shape resembling an ellipse, with the gas treatment chamber 268 substantially positioned at a focal-point of the ellipse.

In some embodiments, the UV radiation source or the magnets reside outside the gas treatment chamber. Where the UV radiation source resides outside the gas treatment chamber, the chamber housing should permit transmission of substantial amounts of UV light into the gas treatment chamber. For example, a glass tube comprising GE Type 214 fused quartz glass is an appropriate gas treatment chamber housing where the UV radiation source resides outside the gas treatment chamber.

A second embodiment water treatment device 226 connected to a water reservoir 224 of a water system is illustrated in FIG. 7. The water system of FIG. 7 is typically, but not limited to a cooling tower water system. Other water systems for which a second embodiment water treatment device is an appropriate treatment device include, but are not limited to, swimming pools, hot tubs, heat exchangers, chillers, process recirculation systems, point-of-entry water treatment systems, petroleum and gas production systems, feedlot water systems, architectural water systems, agricultural water systems, and recreational water systems.

The water treatment device 226 is operationally coupled to the water reservoir 224 through a gas outlet tube 265. The water reservoir is in fluid communication with the water treatment device through the gas outlet tube. In typical operation, the water treatment device delivers treated gas to the water reservoir through the gas outlet tube, and water from the water system does not enter the water treatment device. The gas is typically, but not necessarily, air.

Figure 8:
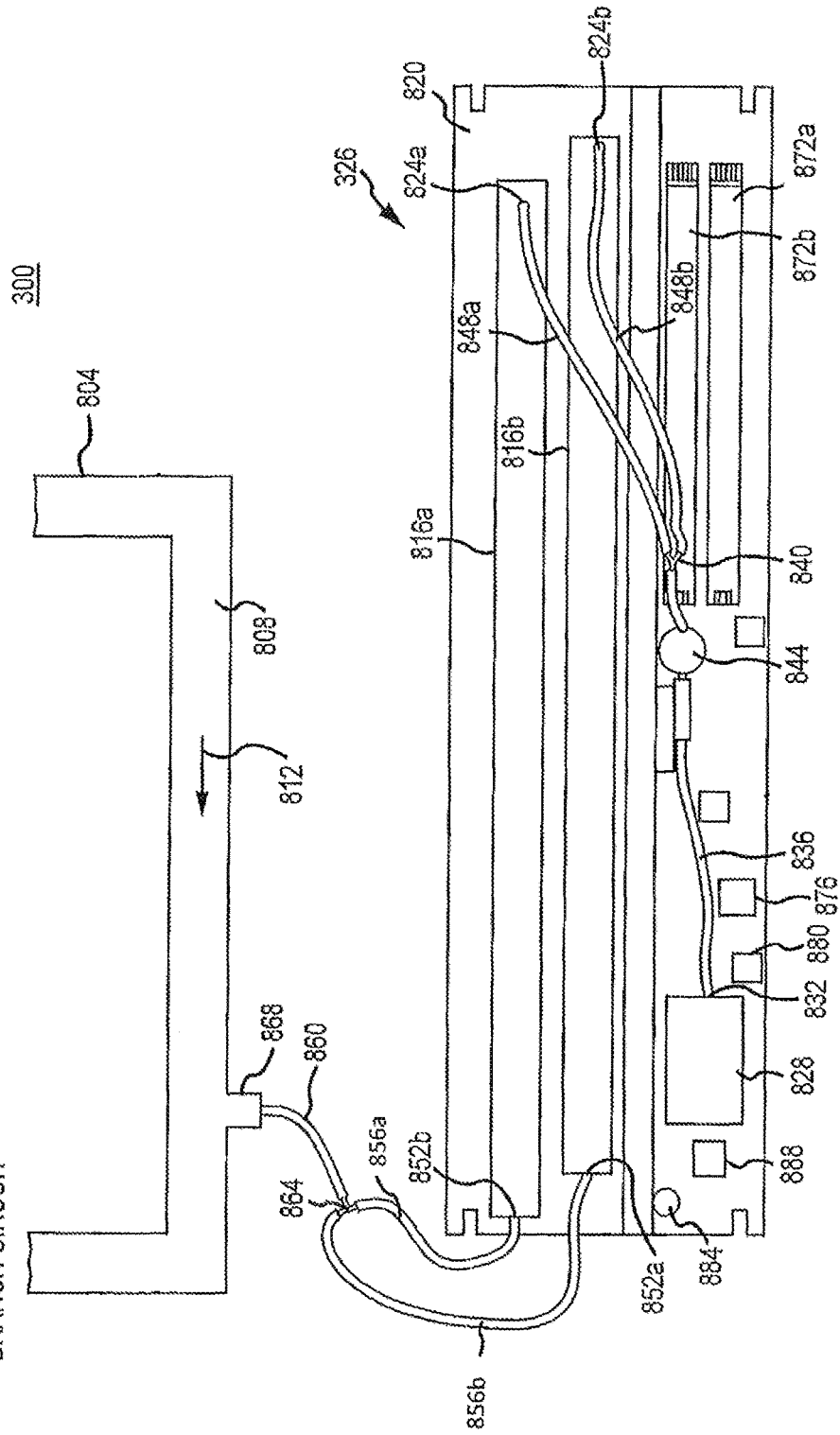
FIG. 8 depicts a water treatment system in accordance with embodiments of the present disclosure.

A water treatment system 300 incorporating a water treatment device 326 in accordance with further embodiments of the present disclosure is illustrated in FIG. 8. In this embodiment, the water treatment device 326 provides a treated gas to a water containing system. The treated gas can comprise an oxygen containing gas such as air from the ambient environment that has been exposed to ultraviolet radiation in a treatment chamber, and that is then introduced to water in the water containing system. In accordance with further embodiments, the treated gas can comprise air that has been exposed to ultraviolet radiation in the presence of a magnetic field within a treatment chamber, and that treated gas can then be introduced to water in the water containing system. In the illustrated embodiment, the water treatment device 326 is interconnected to a branch circuit or line 804 of a system containing water 808. The system containing water 808 can comprise any water containing system. Examples of water that can be treated using embodiments of the disclosed invention include cooling tower water, recreational water, therapy water, architectural water, water used in oil and gas production, and agricultural water. In general, the water treatment device 326 can be associated with any system containing water that requires or that can benefit from treatment of the water by introducing a gas treated by a water treatment device 326 as disclosed herein. In addition, although shown as being connected to a branch circuit or line 804, treated gas produced by a water treatment device 326 in accordance with embodiments of the present invention can be introduced directly to a main reservoir or body of water within a system 808.

The water treatment device 326 generally includes at least one treatment chamber 816 that contains a UV radiation source. In addition, the treatment chamber 816 can house one or more magnets, configured in one or more arrays. An oxygen gas, such as ambient air, is introduced by an inlet 824 to the treatment chamber 816, for example by a pump 828 or other source of pressurized gas. After exposure to the UV radiation and, optionally, to the magnetic field, the treated gas exits the treatment chamber 816 through an outlet 852, and is introduced to the water 808 contained within the system 808. In this particular example, the water is circulated through the branch circuit 804 in the direction of arrow 812.

A water treatment device 326 can include any number of treatment chambers 816, for example to scale the water treatment device 326 such that an appropriate amount of treated gas can be provided to the system containing water 808 to be treated. The water treatment device 326 in the exemplary embodiment of FIG. 8 includes multiple treatment chambers 816. In particular, first 816a and second 816b treatment chambers are illustrated. The treatment chambers 816 are mounted to a common frame or support structure 820. Each treatment chamber 816 includes an inlet 824 that is supplied with pressurized air by a pump 828. More particularly, an outlet 832 of the pump 828 can be connected to a common supply conduit 836. The common supply conduit 836 can in turn be connected to a Y or T fitting 840 via a solenoid valve 844. First 848a and second 848b supply conduits are interconnected to the first 824a and second 824b inlets of the treatment chambers 816a and 816b respectively. In accordance with embodiments of the present disclosure, the pump 828 draws air from the ambient environment, and provides a pressurized supply of such air to the treatment chambers 816. The solenoid valve 844 allows the interior volumes of the treatment chambers 816 to be sealed off while the pump 828 is not supplying pressurized air, for example as a result of a planned or inadvertent shutdown of the pump 828, to prevent a backflow of water into the water treatment device 326.

Each treatment chamber 816 includes an outlet 852. Each outlet 852 can be interconnected to a corresponding outlet conduit 856a or 856b. The outlet conduits 856 are in turn interconnected to a common outlet conduit 860 by a Y or T fitting 864. The common outlet conduit 860 is in turn interconnected to the branch circuit 804 at an injection port 868. Accordingly, pressurized air that is passed through a treatment chamber 816 is supplied to the water within the branch circuit 804 as a treated gas via the injection port 868. In accordance with at least some embodiments, the injection port 868 can comprise a simple T fitting, a bubbler, a venturi, or the like. Alternatively or in addition, the injection port 868 can incorporate or be associated with a one-way valve that allows treated gas to enter the flow of water, but to prevent that water from entering the outlet conduit 860. Moreover, the injection port 868 can incorporate or be associated with a viewing port, for example to allow maintenance personnel to confirm operation of the device by inspection.

The water treatment device 326 also includes various electronic components. For example, a ballast 872 is provided to supply a controlled current to the UV radiation or light source 912 (see FIG. 9) within each treatment chamber 816. In the example illustrated in FIG. 8, a first ballast 872a is provided to supply current to the UV radiation source 912 of the first treatment chamber 816a, while a second ballast 872b is provided to supply a controlled current to the UV radiation source 912 of the second treatment chamber 816b. In addition, one or more controller boards 876 may be provided. The controller board 876 can include a processor and associated memory to control aspects of the operation of the water treatment device 326. For example, operation of the pump 828, the solenoid 844, and the UV radiation sources 912 can be under the control of the controller board 876. The controller board 876 can also receive control input, for example from a user through an associated user input device 880 regarding the operation of the water treatment device 326. Moreover, the controller board 876 can provide output to a user output device 884 concerning the operation of the water treatment device 326. In an exemplary embodiment, the controller board 876 may comprise a controller device with an integrated processor and memory. Alternatively or in addition, the controller board 876 can include discrete digital logic devices and/or analog devices. Embodiments of a water treatment device 326 can additionally include various gages and/or indicator lamps 888. The gages and indicator lamps 888 can include indications of the amount of current being drawn by one or more of the UV radiation sources 912, to provide an indication of the proper operation of the UV radiation source 912. As a further example, a gage or indicator lamp 888 can provide indication of the air pressure within a treatment chamber 816, to provide information regarding the operation of the pump 828.

Figure 9:
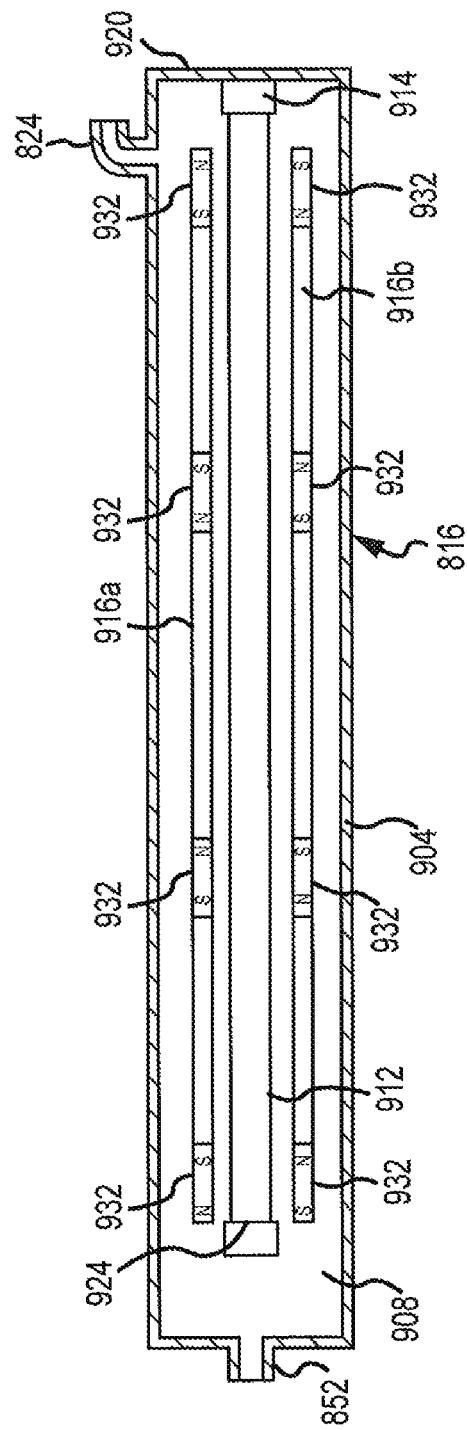
FIG. 9 is a cross-section of a treatment chamber in accordance with embodiments of the present invention.

FIG. 9 is a cross-section of a treatment chamber 816 in accordance with embodiments of the present disclosure. The treatment chamber 816 includes a treatment chamber housing 904. The treatment chamber housing 904 includes a treatment chamber input port or inlet 824 and an a treatment chamber output port or outlet 852. The treatment chamber housing 904 additionally defines an interior or treatment volume 908. Moreover, the input port 824 and the output port 852 are generally at opposite ends of the treatment chamber housing 904 and the interior volume 908 defined therein. An ultraviolet (UV) radiation or light source 912 is located within the interior volume 908 of the treatment chamber housing 904. The UV radiation source 912 can comprise a low pressure mercury lamp that produces light at germicidal (e.g., about 254 nm) and ozone producing (e.g., about 180 nm) wavelengths. Moreover, the UV radiation source 912 can, in an exemplary embodiment, but without limitation, comprise a four pin single ended device, with the pins or electrical contacts located in a base portion 914 at a first end 920 of the treatment chamber housing 904. As can be appreciated by one of skill in the art, in a single ended lamp, the power is supplied to an electrode or electrodes at the second end 924 of the lamp by wires (not shown) that extend from the first end 920 to the second end 924 of the lamp. In accordance with still other embodiments, the UV radiation source 912 can comprise any source of radiation at the desired wavelength or wavelengths. For example, a UV radiation source 912 can comprise one or more lasers tuned or otherwise configured to output a desired wavelength or wavelengths.

The treatment chamber 816 can also include a pair of linear arrays 916 of magnets 932. The magnets 932 can be arranged such that the polarities of the individual magnets 932 within an array 916 repel one another. In addition, as between the two arrays 916a and 916b, adjacent magnets 932 are arranged such that their magnetic fields are oppositely aligned. Alternatively, the magnets 932 can be arranged such that the polarities of the individual magnets 932 with the array 916 attract one another. In addition, as between the two arrays 916a and 916b, adjacent magnets 932 are arranged such that their magnetic fields similarly aligned.

As a result, magnetic fields that traverse at least some or a substantial portion of the interior volume 908 of the treatment chamber 816 are created. Depending upon the arrangement of magnets 932 within the individual arrays 916a and 916b and the arrangement of arrays 916a relative to 916b, the magnetic fields may be substantially attractive (that is, substantially between magnetic North and South poles) or substantially non-attractive (that is, substantially between one of magnetic North poles or one of magnetic South poles).

Accordingly, air introduced at the inlet 824 and exhausted through the outlet 852 is passed through the magnetic fields, as well as being exposed to UV radiation from the UV radiation source 912. The UV radiation source 912 can be any electromagnetic source providing electromagnetic radiation having wavelengths of one or both of 180 and 254 nm. It can be appreciated that the UV radiation source 912 can, in addition to one or both of 180 and 254 nm wavelengths, provide electromagnetic radiation of other wavelengths. The UV radiation source 912 can be electromagnet energy provided by diodes, the sun or any other source capable of producing electromagnetic energy of one or both of 180 and 254 nm.

The electromagnetic energy can be focused and/or directed in the chamber 816 by one or more of reflective surfaces, transparent surfaces, lenses, light pipes, combinations thereof or such. Furthermore, the air may be exposed to thermal energy as well as UV radiation. The exposure to the thermal energy may raise or lower the temperature of the air. A thermal energy source may be used in place of UV radiation source 912.

In accordance with alternate embodiments, the magnets 932 within an array 916 can be arranged such that they attract one another. In accordance with still further embodiments, magnets can be placed next to the ends of the UV radiation source 912. For example, a pair of magnets 932, aligned such that their magnetic fields are opposite one another, can be placed next to each end of the UV radiation source 912. The magnets 932 can comprise permanent magnets, including but not limited to high strength permanent magnets. Alternatively or in addition, the magnets 932 can comprise electromagnets. In accordance with still other embodiments, magnets 932 can be located outside of the treatment chamber 816, but positioned such that the magnetic field or fields produced by the magnets 932 intersect gas that will be provided to the water to be treated as a treated gas.

As can be appreciated by one of skill in the art after consideration of the present disclosure, a water treatment device 326 can be scaled to incorporate any number of treatment chambers 816. For example, a single treatment chamber 816 version can be provided by omitting the second treatment chamber 816b, and by likewise omitting the associated conduits 848b and 852b and the corresponding Ts 840 and 864, or alternatively by capping or plugging the third port of the Ts 840 and 864. As yet another alternative, a water treatment device 326 can incorporate more than two treatment chambers 816, by providing additional treatment chambers 816, and through appropriate interconnections of the inlets 824 of such chambers 816 to the pump 828, and between the outlets 852 of such chambers and the injection port 868. In accordance with still other embodiments, a water treatment device 326 can be provided with multiple treatment chambers 816, in which less than all of the treatment chambers 816 are operated. For example, additional treatment chambers 816 can be incorporated as spares, and can be interconnected to the pump 828 and the injection port 868 after the failure of another one of the treatment chambers 816. In accordance with still other embodiments, a water treatment device 326 with multiple treatment chambers 816 can be provided in which all of the included treatment chambers 816 are interconnected to the pump 828 and/or oxygen concentrator and to the injection port 868, but in which a selected number of UV radiation sources 912 associated with treatment chambers 816 are operated at any particular point in time. Further in accordance with still other embodiments, the water treatment device 326 may include a gas humidifier or a gas de-humidifier to supply, respectively, one of humidified or de-humidified gas to the treatment chambers 816. Such embodiments permit higher concentrations of treated gas to be supplied to the injection port 868 when required, by operating all or a greater number of the treatment chambers 816, for example upon startup of the water treatment device 326 or when aggressive treatment of the water 808 within the water treatment system 300 is desired. When a steady state or when aggressive treatment of the water 808 is otherwise not required, at least some of the UV radiation sources 912 can be powered off, to conserve electrical power.

Figure 10:
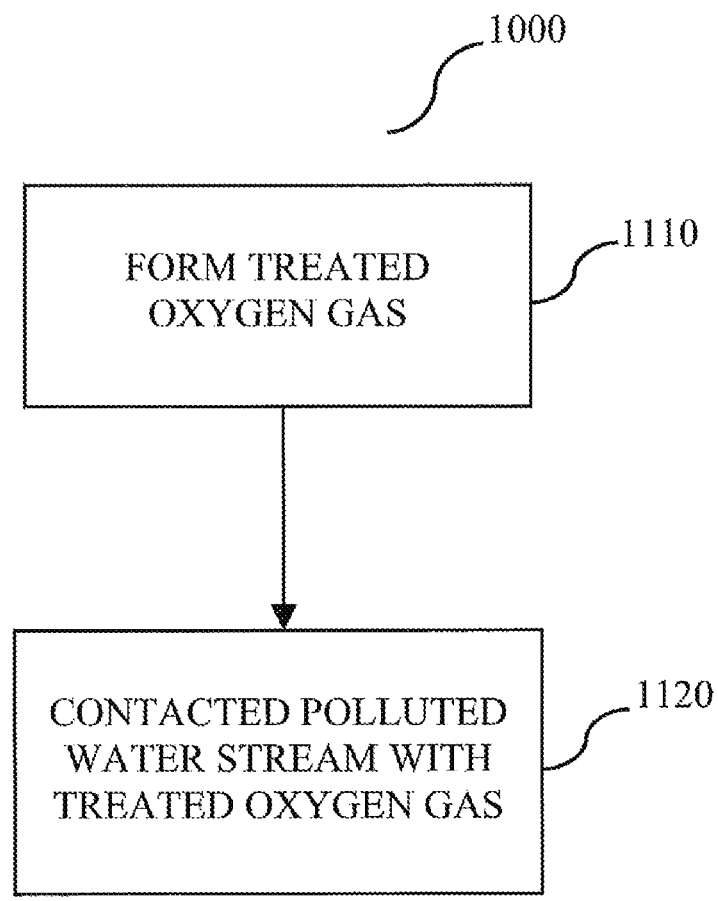
FIG. 10 is a flowchart depicting aspects of a method for treating water in accordance with embodiments of the present invention.

FIG. 10 depicts a process 1000 for treating a water stream in accordance with some embodiments of the present disclosure.

In step 1110, an oxygen-containing gas stream is contacted with ultraviolet radiation to form treated oxygen gas.

Preferably, the oxygen-containing gas stream comprises air. The air can be derived from any source, such as without limitation the surrounding atmosphere, a compressor, an air pump, or a gas cylinder containing compressed air to name a few. In some configurations, the oxygen-containing gas stream can comprise an oxygen fortified air or a super-atmospheric oxygen gas stream. Oxygen fortified air generally refers to gas stream containing more than about 21.1% oxygen ($O_2$) (according to the 1976 Standard Atmosphere) and nitrogen ($N_2$), argon (Ar) and carbon dioxide ($CO_2$) in volume ratio of about 78:1:0.04. At least some of the oxygen contained in the oxygen fortified air can be derived from an oxygen concentrator, oxygen-generator, and/or oxygen source (such as without limitation, bottled oxygen gas or liquid oxygen source). A super-atmospheric oxygen gas stream generally refers a gas stream having a partial pressure of oxygen greater than the ambient oxygen partial pressure. The supper-atmospheric oxygen gas stream may or may contain one or more of nitrogen, argon and carbon dioxide and may or may not have a nitrogen:argon:carbon dioxide volume ratio of about 78:1:0.04.

The ultraviolet radiation can be derived from any process and/or device generating ultraviolet electromagnetic radiation. Preferably, the oxygen-containing gas stream absorbs at least some the ultraviolet radiation to form the treated oxygen gas. More preferably, at least some of the oxygen absorbs at least some of the ultraviolet radiation to form the treated oxygen gas. In some configurations, the oxygen-containing gas stream is contacted with the ultraviolet radiation in the presence of an induced magnetic field.

The induced magnetic field is generated by a linear array of magnets. The magnets are preferably permanent magnets, but in some configurations can be electromagnets.

The ultraviolet radiation has a wavelength from about 40 to about 400 nm. Preferably, the ultraviolet radiation comprises radiation having a wavelength of about 180 nm, about 254 nm, or a mixture of 180 and 254 nm wavelengths.

While not wanting to be limited by theory, it is believed that the treated oxygen gas comprises oxygen atoms. The absorption of ultraviolet radiation by oxygen ($O_2$) is believed to cause some of the oxygen ($O_2$) to dissociate into oxygen atoms (O). The oxygen atoms (O) are believe to be oxygen neutral, that is uncharged, oxygen radials.

In step 1120, a water stream is contacted with the treated gas to form a treated water stream. In some configurations, the water stream has a first concentration of bacteria and the treated water has a second concentration of bacteria. Preferably, the second concentration is no more than the first concentration.

In a method of treating water by use of a water treatment device of the present invention, the electric gas pump of at least some embodiments of the water treatment device draws air from within the housing of the water treatment device and pumps the air under positive pressure through the fluid delivery tube. The air flows across a pressure gradient into the gas treatment chamber, where the air is subjected to UV radiation while proximate a magnet residing in the magnetic rod. The gas is preferably UV irradiated while within 8 inches of the magnet, more preferably within 3 inches of the magnet, still more preferably within 1.5 inch of the magnet, and most preferably within 0.5 inch of the magnet. The UV radiation is emitted by the UV radiation source. The UV radiation source of the second embodiment water treatment device emits radiation having spectral peaks with wavelengths of approximately 253.7 nm and 180 nm.

As used here, even lasers and diodes can emit radiation having spectral peaks, although the spectrum or spectrums of radiation may be very narrow. Persons of ordinary skill in the art recognize that even radiation referred to as monochromatic usually emits a wavelengths across a spectrum, albeit a very narrow one. Where a UV radiation source emits radiation of only one wavelength, that wavelength is considered a spectral peak for the purposes of this specification and appended claims.

Ozone is generated in the air as it flows through and is treated in the gas treatment chamber. The treated air exits the gas treatment chamber into the gas outlet tube and then into the water reservoir. Air that exits the water treatment device by flowing into the gas outlet tube is replaced by air flowing into the housing through gas inlet ports disposed in the water treatment device housing.

Treated air refers to air that has been irradiated by UV light from the UV radiation source in the presence of a magnetic field generated by the magnets. In the second embodiment of the water treatment device, the magnets are permanent magnets. In some other embodiments, the magnets can be electromagnets. In accordance with still other embodiments, a combination of electromagnets and permanent magnets can be included. Moreover, where permanent magnets are used, those magnets can comprise high strength magnets. Air that exits the water treatment device by flowing into the gas outlet tube is replaced by air flowing into the housing through gas inlet ports.

While not wanting to be limited by any particular example, the presence and orientation of magnetic fields within the treatment chamber when oxygen-containing gas is exposed to ultraviolet light can affect the level of hydrogen peroxide in the treated water. Table II summarizes the effect that a magnetic field can have on the level of hydrogen peroxide in the treated water. In Test No. 1, a 20-gallon sample of water was exposed for 20 minutes to

TABLE II

| Test No. | Magnetic Configuration | Level of $H_2O_2$ in Treated Water |
|---|---|---|
| 1 | No Magnetic Field | 0.2 ppm |
| 2 | (NS)(NS)(NS)(NS) | 1.0 ppm |
| 3 | (NS)(SN)(NS)(SN) | 4.0 ppm | an oxygen-containing gas treated with ultra-violet light in the absence of an applied magnetic field. At the conclusion of Test No. 1, the treated water had a hydrogen peroxide level of about 0.2 ppm. In Test No. 2, a fresh 20-gallon sample of water was exposed for 20 minutes to an oxygen-containing gas treated with ultra-violet light in the presence of an attractive magnetic field. The attractive magnetic field is formed from a series of magnets having their magnetic poles aligned in an attractive manner, that is (NS)(NS)(NS)(NS). The water treated with oxygen-containing gas radiated with ultra-violet light in the presence of the attractive magnetic field had a hydrogen peroxide level of about 1.0 ppm at the conclusion of Test No. 2, about five times that of the water treated in the absence of an applied magnetic field. In Test No. 3, a fresh 20-gallon sample of water was exposed for 20 minutes to an oxygen-containing gas treated with ultra-violet light in the presence of an opposing magnetic field. The opposing magnetic field is formed from a series of magnets having their magnetic poles aligned in an opposing manner, that is (NS)(SN)(NS)(SN). Water treated with oxygen-containing gas radiated with ultra-violet light in the presence of the opposing magnetic field had a hydrogen peroxide level of about 4.0 ppm at the conclusion of Test No. 3. This is about twenty times that of water treated in the absence of an applied magnetic field and about four times that of water treated with an applied attractive magnetic field.

Water treated with the water treatment device can have a reduced surface tension compared to untreated water. While not wanting to be limited by any particular example, the footprint of a drop of water on a control substrate prior to treatment was about half that of a drop of water after being treated by the treatment device. It is believed that the doubling in size of the footprint of the treated water is substantially due to a decrease in the surface tension of the treated water.

In some embodiments, the water treated by the water treatment device is cooling tower water. Preferably, the cooling tower water is a re-circulated cooling tower water, typically referred to by those of ordinary skill in the art as a closed dry cooling tower water. While not wanting to limited by example the cooling tower water or other water being treated may be a component of an oil refinery, a petrochemical and/or other chemical plant, a power station or a heating, ventilation and air condition system. The water treatment device can be configured to contact treated gas that is a gas contacted with ultra-violet light with the cooling tower water at any location in the cooling water system. Preferably, the treated gas is contacted with, that is injected in the cooling tower header line and/or side stream line interconnected to the cooling tower header line.

In some embodiments, the water treated by the water treatment device is one of recreational, therapy and architectural water. Preferably, the recreational, therapy and/or architectural waters comprise a re-circulating water system. Non-limiting examples of recreational waters include swimming pools, spas and hot tubs. Non-limiting examples of therapy pools include hydrotherapy pools, injury (such as, burn, skeletal, and/or muscular) recovery/rehab pools, low impact exercise pools and such. Architectural waters include without limitation water fountains, water walls, reflective pools and the like. The water re-circulating system for recreational, therapy and architectural waters typically include one or more of the following unit operations: balance tank unit; flocculation process; filtration unit; aeration unit; antimicrobial treatment unit; and sorbent treatment unit. The water treatment device can be configured to contact treated gas that is a gas contacted with ultra-violet light with the recreational, therapy and/or architectural water at any location in the re-circulating water system. Preferably, the water treatment device replaces one or more of the unit operations, such as but not limited to the aeration and antimicrobial units.

In some embodiments, the water treated by the water treatment device is agricultural water. Preferably, the water contains an adjuvant being applied to animals and/or plants to treat the animals and/or plants. In some embodiments, the adjuvant is formulated with water treated by the water treatment device. In some embodiments, the water containing the adjuvant is treated by the water treatment device prior to being applied to the animal and/or plant.

It can be appreciated that the water treatment device as described herein can effectively treat mining waters, refinery waters, offshore drilling platform waters, and industrial chemical process plant waters.

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

What is claimed is:

1. A system for treating water, comprising:
   a treatment chamber housing, wherein the treatment chamber housing defines an interior gas volume;
   a treatment chamber inlet, wherein the treatment chamber inlet is operable to admit an oxygen-containing gas stream into the interior gas volume of the treatment chamber housing;
   an ultraviolet (UV) radiation source having an axis, wherein the UV radiation source is located within the interior gas volume of the treatment chamber housing, and the UV radiation source and interior gas volume are configured such that the oxygen-containing gas stream passes over the UV radiation source;
   a plurality of permanent magnets, wherein the plurality of permanent magnets is located within the interior gas volume of the treatment chamber housing, and the plurality of permanent magnets and interior gas volume are configured such that the oxygen-containing gas stream passes over the plurality of magnets, wherein at least some permanent magnets of the plurality of permanent magnets are arrayed along a line having an axis, wherein the axis of the UV radiation source is substantially parallel with the axis of the line of permanent magnets; and
   a treatment chamber outlet, wherein the treatment chamber outlet is operable to exhaust the oxygen-containing gas stream from the interior gas volume of the treatment chamber housing.

2. The system of claim 1, wherein adjacent permanent magnets of the plurality of permanent magnets are spaced apart by a distance greater than 0".

3. The system of claim 2, wherein adjacent permanent magnets of the plurality of permanent magnets are spaced apart equally from one another.

4. The system of claim 1, wherein polarities of the permanent magnets arrayed along the line are such that a first permanent magnet attracts a second permanent magnet in the line.

5. The system of claim 1, wherein polarities of the permanent magnets arrayed along the line are such that a first permanent magnet repels a second permanent magnet in the line.

6. The system of claim 1, further comprising:
   a common outlet conduit connected to the treatment chamber outlet; and
   an injection port connected to the common outlet, wherein the injection port is operable to exhaust the oxygen-containing gas stream into a body of water.

7. The system of claim 1, wherein the axis of the UV radiation source and the axis of the line of permanent magnets are noncollinear.

8. The system of claim 1, wherein at least some of the permanent magnets of the plurality of permanent magnets are positioned proximate to at least one of a first end of the UV radiation source and a second end of the UV radiation source.

9. The system of claim 1, further comprising at least one of:
   an air pump, wherein an outlet of the air pump provides a flow of air to the treatment chamber inlet; and
   one of a source or generator of the oxygen-containing gas stream.

10. The system of claim 1, wherein a plurality of UV radiation sources is located within the interior gas volume of the treatment chamber housing.

11. A system for treating water, comprising:
- a treatment chamber housing, wherein the treatment chamber housing has an inner surface and defines an interior volume;
- a treatment chamber inlet, wherein the treatment chamber inlet is operable to admit an oxygen-containing gas stream into the interior volume of the treatment chamber housing;
- an ultraviolet (UV) radiation source having an outer surface, wherein the UV radiation source is located within the interior volume of the treatment chamber housing, wherein a first space is defined between at least part of the outer surface of the UV radiation source and the inner surface of the treatment chamber housing, and the oxygen-containing gas stream is configured to pass through the first space;
- a plurality of permanent magnets, wherein each permanent magnet has an outer surface and the plurality of permanent magnets is located within the interior volume of the treatment chamber housing, wherein a second space is formed between at least part of the outer surfaces of the permanent magnets and the inner surface of the treatment chamber housing, and the oxygen-containing gas stream is configured to pass through the second space; and
- a treatment chamber outlet, wherein the treatment chamber outlet is operable to exhaust the oxygen-containing gas stream from the interior volume of the treatment chamber housing.

12. The system of claim 11, wherein adjacent permanent magnets of the plurality of permanent magnets are spaced apart by a distance greater than 0".

13. The system of claim 12, wherein adjacent permanent magnets of the plurality of permanent magnets are spaced apart equally from one another along an axis.

14. The system of claim 11, wherein polarities of the permanent magnets arrayed along a line are such that a first permanent magnet attracts a second permanent magnet in the line.

15. The system of claim 11, wherein polarities of the permanent magnets arrayed along a line are such that a first permanent magnet repels a second permanent magnet in the line.

16. The system of claim 11, further comprising:
- a common outlet conduit connected to the treatment chamber outlet; and
- an injection port connected to the common outlet, wherein the injection port is operable to exhaust the oxygen-containing gas stream into a body of water.

17. The system of claim 11, wherein the UV radiation source is disposed along a first axis, and at least some of the permanent magnets of the plurality of permanent magnets are arrayed along a second axis, wherein the first axis and the second axis are noncollinear.

18. The system of claim 11, wherein at least some of the permanent magnets of the plurality of permanent magnets are positioned proximate to at least one of a first end of the UV radiation source and a second end of the UV radiation source.

19. The system of claim 11, further comprising at least one of:
- an air pump, wherein an outlet of the air pump provides a flow of air to the treatment chamber inlet; and
- one of a source or generator of the oxygen-containing gas stream.

20. The system of claim 11, wherein a plurality of UV radiation sources is located within the interior volume of the treatment chamber housing.

* * * * *